United States Patent
Peak et al.

(10) Patent No.: US 9,558,520 B2
(45) Date of Patent: Jan. 31, 2017

(54) SYSTEM AND METHOD FOR GEOCODED INSURANCE PROCESSING USING MOBILE DEVICES

(75) Inventors: David F. Peak, Avon, CT (US); Andrew J. Amigo, Gloucester, MA (US); Richard M. Borden, West Hartford, CT (US); Keven J. Busque, Manchester, CT (US); Eugene J. Walters, Avon, CT (US)

(73) Assignee: HARTFORD FIRE INSURANCE COMPANY, Hartford, CT (US)

( * ) Notice: Subject to any disclaimer, the term of this patent is extended or adjusted under 35 U.S.C. 154(b) by 677 days.

(21) Appl. No.: 12/754,189

(22) Filed: Apr. 5, 2010

(65) Prior Publication Data

US 2011/0161116 A1 Jun. 30, 2011

Related U.S. Application Data

(60) Provisional application No. 61/291,501, filed on Dec. 31, 2009.

(51) Int. Cl.
| | | |
|---|---|---|
| *G06Q 40/00* | (2012.01) | |
| *G06Q 40/08* | (2012.01) | |
| *G06F 19/00* | (2011.01) | |
| *G06Q 10/06* | (2012.01) | |
| *G06Q 10/10* | (2012.01) | |
| *G06Q 50/22* | (2012.01) | |
| *G06Q 50/24* | (2012.01) | |

(52) U.S. Cl.
CPC ............. *G06Q 40/08* (2013.01); *G06F 19/323* (2013.01); *G06F 19/3418* (2013.01); *G06F 19/366* (2013.01); *G06Q 10/067* (2013.01); *G06Q 10/10* (2013.01); *G06Q 50/22* (2013.01); *G06Q 50/24* (2013.01)

(58) Field of Classification Search
CPC ....................................................... G06Q 40/08
USPC .......................................................... 705/4
See application file for complete search history.

(56) References Cited

U.S. PATENT DOCUMENTS

| | | | |
|---|---|---|---|
| 5,797,134 A | 8/1998 | McMillan et al. | |
| 6,064,970 A | 5/2000 | McMillan et al. | |

(Continued)

FOREIGN PATENT DOCUMENTS

| | | |
|---|---|---|
| JP | 2002259708 A | 9/2002 |
| JP | 2009005303 A | 1/2009 |
| WO | WO2008120971 A1 * | 10/2008 |

*Primary Examiner* — Eric T Wong
(74) *Attorney, Agent, or Firm* — Howard IP Law Group, PC

(57) ABSTRACT

Pursuant to some embodiments, insurance systems, methods and devices are provided which include a data storage device for storing, updating and providing access to loss risk score data, a computer processor for executing program instructions and for retrieving the loss risk score data from the data storage device, a memory, coupled to the computer processor, for storing program instructions for execution by the computer processor, a geocoding engine comprising program instructions stored in the memory for geocoding historical loss data and a plurality of loss risk factors, a scoring engine comprising program instructions stored in the memory for calculating a loss risk score for each of a plurality of geographical locations based on said historical loss data and said plurality of loss risk factors, and a communication device, coupled to the computer processor, to output loss risk score data based on geographical location.

24 Claims, 25 Drawing Sheets

(56) References Cited

U.S. PATENT DOCUMENTS

| | | | |
|---|---|---|---|
| 6,175,803 B1* | 1/2001 | Chowanic et al. | 701/533 |
| 6,313,791 B1 | 11/2001 | Klanke | |
| 6,714,894 B1 | 3/2004 | Tobey et al. | |
| 6,868,386 B1 | 3/2005 | Henderson et al. | |
| 7,739,133 B1* | 6/2010 | Hail et al. | 705/4 |
| 7,899,823 B1 | 3/2011 | Trandal et al. | |
| 8,090,598 B2 | 1/2012 | Bauer et al. | |
| 8,140,358 B1 | 3/2012 | Ling et al. | |
| 8,255,113 B2 | 8/2012 | Boss et al. | |
| 8,290,705 B2 | 10/2012 | Trinko et al. | |
| 8,311,858 B2 | 11/2012 | Everett et al. | |
| 8,332,242 B1* | 12/2012 | Medina, III | 705/4 |
| 8,416,067 B2 | 4/2013 | Davidson et al. | |
| 8,489,434 B1 | 7/2013 | Otis et al. | |
| 8,527,013 B2 | 9/2013 | Guba et al. | |
| 8,566,126 B1 | 10/2013 | Hopkins, III | |
| 8,577,703 B2 | 11/2013 | McClellan et al. | |
| 8,583,333 B2 | 11/2013 | Rennie et al. | |
| 8,606,512 B1* | 12/2013 | Bogovich | G06Q 40/08 340/995.28 |
| 8,630,768 B2 | 1/2014 | McClellan et al. | |
| 8,655,690 B2 | 2/2014 | Tran et al. | |
| 2002/0111725 A1 | 8/2002 | Burge | |
| 2002/0118118 A1 | 8/2002 | Myllymaki et al. | |
| 2003/0191581 A1* | 10/2003 | Ukai et al. | 701/207 |
| 2004/0128172 A1 | 7/2004 | Van Cleave et al. | |
| 2006/0033615 A1 | 2/2006 | Nou | |
| 2006/0129313 A1 | 6/2006 | Becker et al. | |
| 2006/0136273 A1* | 6/2006 | Zizzamia et al. | 705/4 |
| 2007/0011134 A1* | 1/2007 | Langseth et al. | 707/1 |
| 2007/0173991 A1 | 7/2007 | Tenzer et al. | |
| 2007/0202483 A1 | 8/2007 | Castelli et al. | |
| 2007/0282638 A1* | 12/2007 | Surovy | 705/4 |
| 2008/0065427 A1 | 3/2008 | Helitzer et al. | |
| 2008/0126139 A1* | 5/2008 | Prendergast | G06Q 40/08 705/4 |
| 2008/0189142 A1 | 8/2008 | Brown et al. | |
| 2009/0024419 A1* | 1/2009 | McClellan et al. | 705/4 |
| 2009/0073171 A1 | 3/2009 | Straub et al. | |
| 2009/0138195 A1* | 5/2009 | Pemble et al. | 701/211 |
| 2009/0210142 A1 | 8/2009 | Couckuyt et al. | |
| 2009/0210257 A1 | 8/2009 | Chalfant et al. | |
| 2009/0233572 A1* | 9/2009 | Basir | 455/404.1 |
| 2009/0287401 A1* | 11/2009 | Levine | G01C 21/3492 701/117 |
| 2009/0296605 A1 | 12/2009 | Lewis | |
| 2010/0030582 A1* | 2/2010 | Rippel et al. | 705/4 |
| 2010/0030586 A1* | 2/2010 | Taylor et al. | 705/4 |
| 2010/0063851 A1 | 3/2010 | Andrist et al. | |
| 2010/0070309 A1* | 3/2010 | Deede et al. | 705/4 |
| 2010/0174564 A1 | 7/2010 | Stender et al. | |
| 2011/0040579 A1 | 2/2011 | Havens | |
| 2011/0046920 A1 | 2/2011 | Amis | |
| 2011/0106370 A1 | 5/2011 | Duddle et al. | |
| 2011/0213628 A1 | 9/2011 | Peak et al. | |
| 2012/0158436 A1 | 6/2012 | Bauer et al. | |
| 2012/0209634 A1 | 8/2012 | Ling et al. | |

* cited by examiner

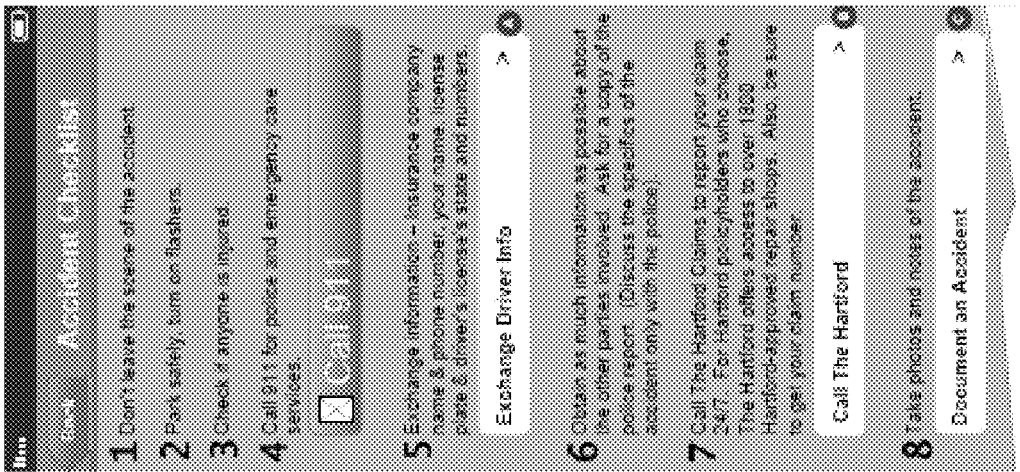
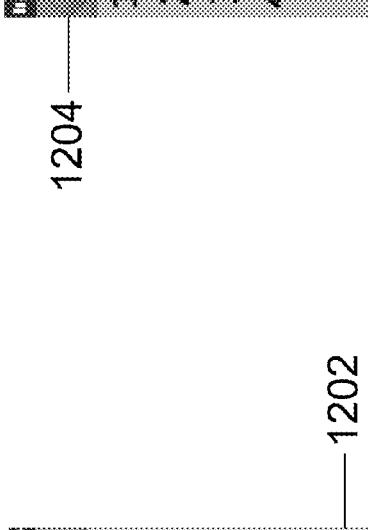
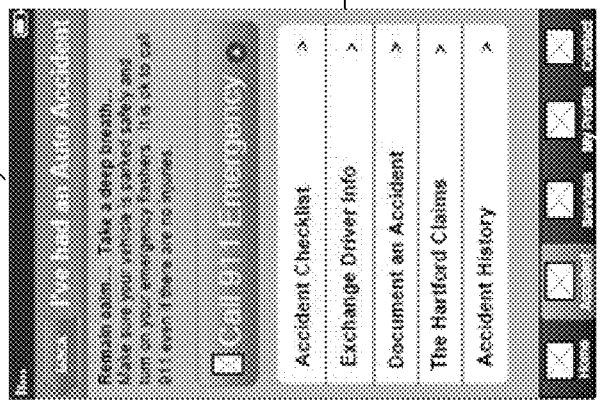
FIG. 12B
FIG. 12A

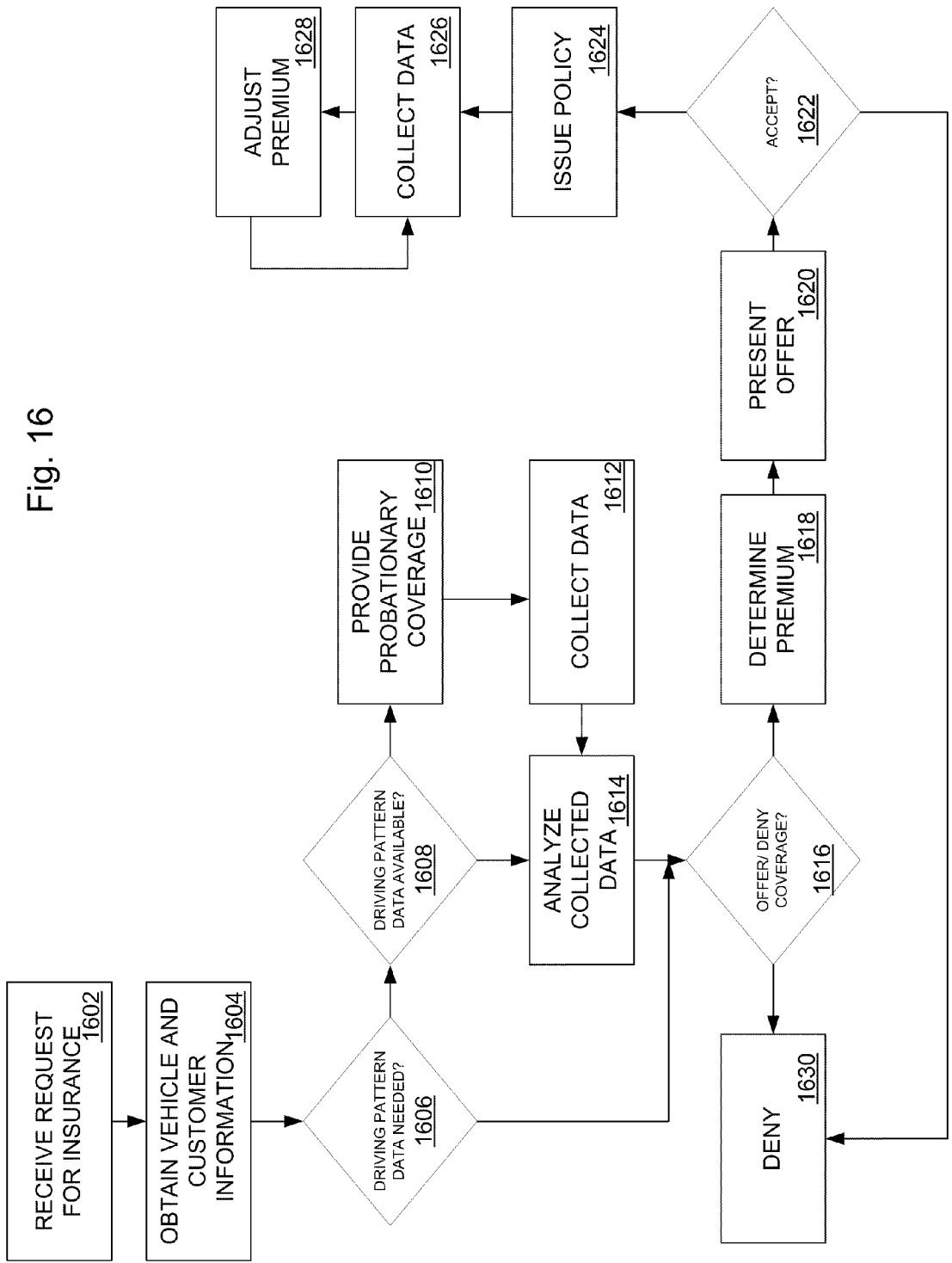

SYSTEM AND METHOD FOR GEOCODED INSURANCE PROCESSING USING MOBILE DEVICES

CROSS REFERENCE TO RELATED APPLICATIONS

The present application is based on, and claims benefit and priority of, U.S. Provisional Patent Application Ser. No. 61/291,501 filed on Dec. 31, 2009, the contents of which are incorporated herein in their entirety for all purposes.

FIELD

Embodiments relate to insurance processing systems and methods. More particularly, embodiments relate to the provision of insurance processing, including loss risk scores and scoring, using mobile devices.

BACKGROUND

Each year, thousands of deaths and millions of injuries result from automobile or other vehicle crashes. Billions of dollars of losses occur as a direct and indirect result of accidents, theft, and injury related to automobiles and other vehicles. It is desirable to reduce those losses and to generally improve the safety of drivers and passengers.

Many accidents and thefts occur in high risk areas. For example, more theft losses may occur in urban areas. Accident-related deaths may occur on certain stretches of suburban roads with difficult to navigate turns or impaired sight lines. Many non-injury accidents occur in high traffic density areas, such as parking lots or shopping areas.

It would be desirable to provide information to vehicle operators to alert them of the existence and location of these higher risk areas so that they can either avoid them or take extra care when operating in those areas. It would further be desirable to provide more accurate and current data about areas which have higher loss risks, including the receipt of accurate information associated with accidents and potential claims. Further still, it would be desirable to monitor or identify driving patterns associated with certain drivers to allow those drivers to receive discounts or other benefits based on desirable driving patterns such as avoiding or reducing time spent operating in high loss risk areas.

BRIEF DESCRIPTION OF THE DRAWINGS

FIG. 12A-J is a series of user interface diagrams depicting mobile device interfaces pursuant to some embodiments.

FIG. 16 is a flow diagram of a process carried out by the system of FIG. 13 for processing requests for insurance.

DETAILED DESCRIPTION

Figure 1:
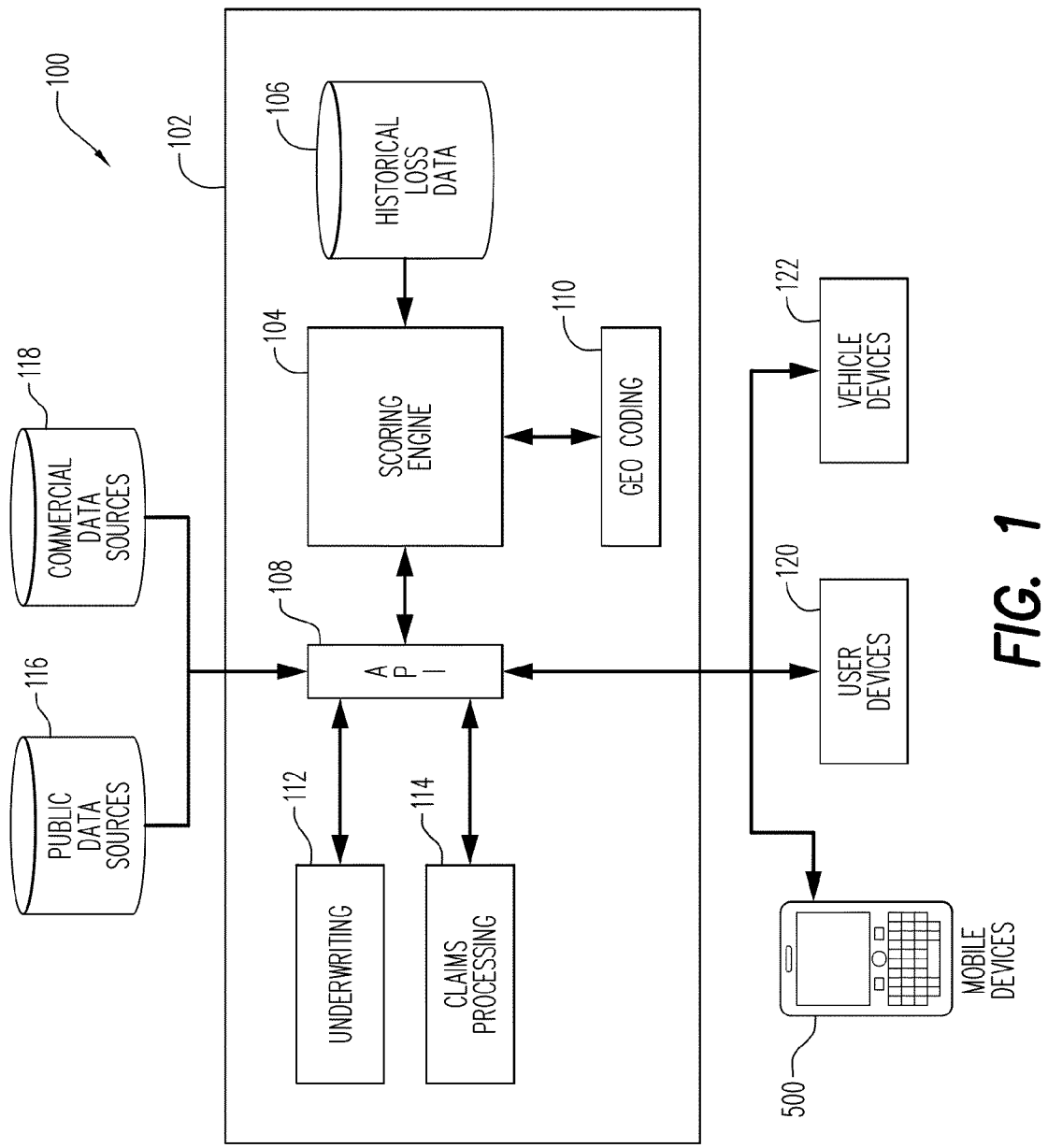
FIG. 1 illustrates a system architecture within which some embodiments may be implemented.

Embodiments of the present invention relate to systems and methods for reducing vehicle related losses, including insurance systems for underwriting policies and processing claims associated with vehicles. Applicants have recognized a need for systems and methods which allow loss data, demographic data, and data related to weather, time of day, day of week, and other data to be used to generate loss risk scores. Pursuant to some embodiments, these loss risk scores are presented to users (such as drivers, insured individuals or other interested parties) via mobile devices to allow those users to avoid or reduce their exposure to high risk areas or locations. Pursuant to some embodiments, users may provide data or other information about accidents, thefts, other losses, or safety information via their mobile devices. This data, in some embodiments, is used to update loss risk scoring data. Features of some embodiments may be used in conjunction with pricing, underwriting, updating and otherwise interacting with insurance providers. In some embodiments, features may be used in conjunction with individual or personal insurance policies as well as fleet or commercial policies. As used herein, the term "pricing" generally refers to the calculation of a premium associated with an insurance policy.

In some embodiments, mobile devices are provided with applications that allow users to easily access, view, and interact with the loss risk data. For example, in some embodiments, users are able to view maps, routes, and other user interfaces having graphical depictions of loss risks by area. The applications, in some embodiments, allow users to submit data used to enhance or update the loss risk score data (e.g., such as by submitting loss claims, reporting on third party accidents, etc.). In some embodiments, the applications further allow the efficient and accurate tracking and reporting of a user's driving or vehicle operation activity, allowing for improved pricing and analysis of insurance policies.

The result is a system and method which provides improved information that may be used to reduce losses and injuries and which provides an improved ability to insure and underwrite individuals and businesses. By providing detailed information about geographical areas which pose a high risk of loss, embodiments allow users to proactively avoid those areas. The accuracy of the information is improved by allowing mobile device users to provide updates about losses and related information while they are at or near an area at which a loss was suffered. Such updates may be used to initiate and process insurance claims associated with a loss. The information may also be used, pursuant to some embodiments, to price and underwrite certain policies, providing improved coverage and pricing for individuals based on their usage and driving patterns.

To introduce features of some embodiments, several illustrative (but not limiting) examples will now be provided. In a first illustrative example, a driver wishes to obtain a new auto insurance policy. The driver has a mobile device (such as a smart phone) that he uses on a daily basis, and the mobile device has built in GPS and wireless features. The driver downloads and installs a mobile application having features of the present invention onto his mobile device from the insurance provider he wishes to obtain coverage from. The driver interacts with the application to provide his insurance application information, including his personal information and details of the vehicle he wishes to obtain coverage for. The application information is transmitted over a wireless network to the insurance provider and an application for insurance is created for the driver. Some or all of the steps in seeking and obtaining coverage are performed using the mobile device installed on the driver's mobile device. Although the application is described as being "downloaded", those skilled in the art will appreciate that the application (and some or all of the data associated with the application) may be pre-installed or preloaded on a device.

In a second illustrative (but not limiting) example, a driver wishes to avoid driving in areas which are dangerous or that have current traffic or driving hazards. The driver downloads and installs a mobile application having features of some embodiments of the present invention onto her mobile device (the application may be the same as the one downloaded by the driver in the first illustrative example, or a different application). The mobile application (having functionality such as that described below in conjunction with FIGS. 4, and 7-10) allows the driver to view her current location (based on GPS or other location data transmitted from her mobile device to a processing system) on a map, as well as to plot out a planned route between locations. In some embodiments, the data may be provided to the user over a network, while in other embodiments, portions of the data may be provided over a network, while other portions may be stored in a storage device associated with the mobile device. Further, while a mobile device may be a mobile telephone, those skilled in the art will appreciate that other devices may receive, consume, and otherwise interact with data of the present invention (e.g., such as mobile GPS devices, vehicle navigation systems, or the like).

The map, according to some embodiments, may include markers or other indicators depicting areas, intersections, streets, or routes which have a higher than average risk of loss. The indicators are created and provided to the mobile device using a scoring engine that includes information about the relative risk of loss associated with different geographical locations or areas. For example, the driver may use the information to decide whether to take one of several possible routes. One of the possible routes may have a higher potential risk of loss or damage than the others, and the driver may elect to take the route with a lower risk of loss. The driver may also use the information to identify parking lots or areas which have lower risks of theft or property damage. Further still, the driver may use the information to identify areas that are currently suffering from higher than ordinary risk (e.g., such as a flooded street that she may want to avoid, or a road under construction, etc.). The driver may also configure the mobile application to alert her (substantially in real time) of upcoming hazards or risks along her route. For example, if the driver is approaching a particularly hazardous intersection (where the intersection has a relatively high risk score) the mobile device may alert her (using visual or audio alerts) that she is nearing a hazardous area. In this way, the driver is able to proactively take steps to reduce her risk of loss or damage. The driver may also interact with the mobile application to submit information about traffic or road conditions that she personally is witness to (for example, to submit information about a particularly dangerous road condition, etc.). This information may be aggregated and provided to other users of the mobile application to provide substantially real time updates to traffic and driving conditions. In some embodiments, additional information may be provided associated with alternative route choices, such as the additional amount of time or distance that one route may require over another.

In a third illustrative (but not limiting) example, a driver wishes to qualify for a discount or reduction in his insurance premium, and agrees to download and install a mobile application that collects data about the driver's driving patterns in order to possibly qualify for a discount or reduction. The driver interacts with the mobile device to allow it to track his driving patterns by allowing the mobile device to collect data about his daily mileage, speed, route, and other information. The data is collected by the mobile device and wirelessly transmitted to an insurance processing system for analysis. The insurance processing system may use the information to determine a relative risk score associated with the driver's driving patterns (e.g., using a scoring engine such as the engine to be described below in conjunction with FIG. 1). The insurance processing system may look at the driver's driving history over a short period of time, or over a longer period of time (e.g., such as for a week, month, or even year) and may adjust the driver's policy pricing based (at least in part) on the driver's driving patterns and the relative risk of the driver's routes, and driving characteristics. The pricing may be adjusted on a going forward basis (e.g., as a reduction to a renewal) or as a discount. In this manner, policies may be priced more accurately and in a manner that reflects a more accurate assessment of the relative risk posed by a driver. In some embodiments, the application may further be used to track where a vehicle is typically parked. Some policies require an insured individual to provide this information. Embodiments of the present invention may allow the data to be automatically collected and transmitted to an insurer for analysis and use.

In a fourth illustrative (but not limiting) example, a driver may suffer an accident or other loss, and may need to submit a claim. Pursuant to some embodiments, the driver may interact with a mobile application to record details about the accident (including taking pictures, recording notes, and entering loss data) using the mobile application. The claim information is then wirelessly transmitted to an insurance processing system for further processing. In some embodiments, the claim information may be automatically appended with time and location data (from the mobile device) for use in processing the claim. In this manner, users may quickly, efficiently and accurately submit claim information. These and other features and embodiments will be described in further detail below.

Features of some embodiments will now be described by first referring to FIG. 1, where a network 100 for providing risk scores and insurance processing pursuant to some embodiments is shown. As depicted, network 100 includes a number of devices which together operate to generate, store and utilize loss risk scores for use in informing users and in insurance processing. Network 100 includes an insurance processing system 102 with a scoring engine 104 that generates loss risk scores that may be provided to a number of users, such as users operating mobile phones 500 (such as those described in conjunction with FIGS. 2, 5 and 6 below), other user devices 120 (such as personal computers or the like), and vehicle devices 122 (such as navigation systems or the like). The loss risk scores may be used to plan routes (e.g., which avoid high loss risk or dangerous areas) and to track driver or vehicle behavior (e.g., to identify driving patterns which present a relatively low or high risk).

Data may be provided from mobile devices 500, user devices 120 and vehicle devices 122 to update data used by the scoring engine 104 to improve the accuracy and relevancy of scoring data. For example, users operating a mobile device 500 may submit information about a vehicle accident, theft, or other information that may be relevant to the generation of loss risk scores. The data may be used by the scoring engine 104 to update loss risk data which may then be disseminated to devices in the network 100. The use of such loss risk data in conjunction with mobile or other devices will be described further below in conjunction with FIGS. 4, and 7-12.

Pursuant to some embodiments, insurance processing system 102 includes a scoring engine 104 which operates on historical loss data 106 and loss-related data from other data sources (such as public data sources 116 and commercial data sources 118) to generate loss risk scores that indicate a relative loss risk. In some embodiments, the loss risk scores (and data used to generate the loss risk scores) are geocoded to create a loss risk index that represents the relative risk of loss in different geographical locations. Pursuant to some embodiments, address and location data may expressed (or "geocoded") as a location (or "geocode") given in latitude and longitude, using standard decimal degrees notation for the latitudes and longitudes, although other spatial and locational data may also be used to code and tag data associated with the present invention.

In some embodiments, the geocoding or tagging may include identifying specific types of locations, such as street intersections, parking lots, or the like so that loss risk scores and other information may be associated with those locations. In some embodiments, system 102 includes a geocoding engine 110 which operates on received data to express the data as a location. For example, the geocoding engine 110 may be used on address data received from an insurance application, claim or other information and translate or express the address as a latitude and longitude. The engine 110 may also append other location-related data to the address data to provide additional location information to the data. The "geocoded" data may then be stored, used as an input to the scoring engine 104, or presented to a user device (e.g., such as a mobile device 500, etc.) for use (e.g., such as by presenting the data in a map format or overlay).

In some embodiments, some of the data used by the scoring engine 104 and/or the geocoding engine 110 may be obtained using data mining techniques (e.g., such as text mining). For example, some claims data or public data used in conjunction with the scoring engine 104 may not be available in a structured format that allows ready geocoding. In such situations, data mining techniques may be used to locate, identify and extract location and risk-relevant data for use and manipulation by the system 102.

Any of a number of different algorithms may be used to generate the loss risk scores and the loss risk index. In some embodiments, the historical loss data 106 and other input data sources 116, 118 are selected based on variables that have a high correlation to loss. The loss risk scores and the loss risk index may be generated using statistical modeling techniques such as by performing computations using discrete scores that are weighted in nonlinear combination (e.g., such as based on the likelihood of a loss in a given geographical location or geocode). In some embodiments, the generation of the loss risk scores and index may be performed by sampling data (including historical loss data 106), normalizing the data, generating a scoring model and verifying and updating the model. In some embodiments, the model may be updated based on actual loss data received from mobile devices and from other sources. In some embodiments, the scoring may be shared among a number of insurance entities (e.g., such as a consortium or group of insurance companies) and historical and current loss data may be provided from those entities to create a more accurate and predictive score.

As a specific example (which is provided for illustration but not limitation), the system of the invention operates on data to generate loss risk scores that are associated with the likelihood of a vehicle loss. In such an example implementation, the following types of data may be used as inputs to the scoring engine: (i) data from historical loss data 106 including historical data associated with collision losses, historical data associated with theft losses, and historical data associated with personal injury losses, (ii) data from public data sources 116, including census and demographic data (e.g., such as population density, crime statistics, emergency call data, highway and road construction data), and (iii) data from commercial data sources 118 (e.g., such as data from other insurers regarding losses, theft data from sources such as LoJack® or OnStar®, and traffic and traffic density data from sources such as EZ-Pass® or the like). This data may further be enhanced or updated using data from users operating mobile devices 500, other user devices 120 and vehicle devices 122 (e.g., such as transponders or communication devices installed in fleet or private vehicles).

A number of algorithms may be used to generate loss risk scores pursuant to some embodiments. As one illustrative (but not limiting) example, a loss risk score may be calculated using the following general function:

$$\text{Loss Risk Score} = aP \times bQ \times cS \times dT \times eU \times fV$$

Pursuant to some embodiments, the function generates a Loss Risk Score which is a score for a specific location or geocode. The Loss Risk Score may be a representation of a general loss risk range. For example, in some embodiments, loss risk tiers may be represented as color codes, such as "green" for low risk, "orange" for normal risk, and "red" for higher risk. As another example, the loss risk tiers may be represented as alphabetical grades or scores (e.g., such as "A" for low risk, "B" for normal risk, and "C" for higher risk). Other representations may include tiers based on percentages, or other representations of the relative risk of a geocode or location.

In the formula depicted above, the variable "P" represents the Average Claims or Loss Severity for a particular geocode or area. The variable "Q" represents the Average Claims or Loss Frequency for that geocode or area. The variable "R" represents a Weather Risk factor (e.g., representing adverse weather conditions, such as a snowstorm, rain storm, hurricane, etc.), and the variable "S" represents a Time of Day risk factor (e.g., associated with a time of day, such as rush hour, night time, etc.) The variable "T" represents a Day Risk Factor (e.g, such as a particular day of the week, holiday, etc.), and the variable "U" represents a Traffic Condition Risk factor (e.g., such as a current traffic condition for a particular geocode or location). The variable "V" represents a User Generated risk factor (based on, for example, inputs received from people reporting or identifying dangerous events or conditions using their mobile devices). The variable "W" represents a Crime Risk factor (e.g., such as a risk of car thefts or property damage). The variable "Y" represents a People or Vehicle risk factor (e.g., based on population density information). Those skilled in the art will appreciate that other variables and inputs may be provided to generate a risk score that has a high correlation to the risk of loss in a particular location or geocode. Each of the variables may be based on data received substantially in real time from a number of different sources. Individual risk factors will only be used in applicable jurisdications as allowed by law.

Pursuant to some embodiments, a trip risk score may be generated using a formula such as:

$$\text{Trip Risk Score} = x\ \%\times A + y\ \%\times B + z\ \%\times C$$

Where the Trip Risk Score is a score for a particular trip or route traveled by an individual or group of individuals across a number of geocodes. The Trip Risk Score may be represented as a color, grade, or other representation of the relative risk associated with a particular trip or route. For example, a high risk route may be represented by a red color, a "C", or a percentage, while a low risk route may be represented by the color green, an "A", or a percentage, while a normal risk route may be represented by the color orange, a "B" or a percentage. Those skilled in the art will appreciate that a number of other representations may be used to depict the relative risk of a trip or route.

In the Trip Risk Score formula depicted above, the variable x % is the percentage of the total trip or route distance (such as in miles) that go through geocodes or locations having a Loss Risk Score of A (or a low risk), while y % is the percentage of the total trip or route distance that pass through geocodes or locations having a Loss Risk Score of B (a normal risk), while z % is the percentage of the total trip or route distance that pass through geocodes or locations having a Loss Risk Score of C (a high risk).

Pursuant to some embodiments, a Vehicle or Person Risk score may also be calculated using a formula such as the following:

$$\text{Vehicle or Person Risk Score} = m\ \%\times A + n\ \%\times B + p\ \%\times C$$

Where the Vehicle or Person Risk Score is a score for a particular person or vehicle (or group of persons or vehicles) over a period of time based on cumulative trips taken during that period of time. For example, a person who, during the course of the year 2010, spends much of their time driving through high risk geocodes may be assigned a Person Risk Score of "red" (or some other indicator of high risk) based for 2010. In the Vehicle or Person Risk Score formula shown above, the variable m % is the percentage of the total distance taken through or in geocodes having a Loss Risk Score of "A" (low risk), n % is the percentage of the total distance taken through or in geocodes having a Loss Risk Score of "B" (normal risk), and p % is the percentage of the total distance traveled in or through geocodes having a Loss Risk Score of "C" (high risk).

Each of these risk scores may be used in providing information to users operating mobile devices as well as in providing insurance services, including in the pricing and underwriting of insurance policies. In some embodiments, the risk scores may be generated and used by an insurance processing system 102.

Insurance processing system 102 may be operated by, or on behalf of, an insurance company that issues insurance policies associated with the type of risk scored by the scoring engine 104. For example, in the situation where the scoring engine 104 is used to score vehicle or automobile types of loss risks, the insurance processing system 102 may be operated by an automobile insurer. In some embodiments, some or all of the components of the system 102 may be operated by or on behalf of other entities. For example, in some embodiments, the system 102 may be operated by a device manufacturer (e.g., such as vehicle navigation system, by a mobile device manufacturer, etc) in order to provide risk and driving related data to their customers. In some embodiments, some or all of the system 102 may be operated by agents or other groups or entities in order to provide, use, and otherwise interact with scoring and driving data pursuant to the present invention.

Data generated by the scoring engine 104, or received from mobile devices 500, user devices 120 and/or vehicle devices 122 may be used by the insurance processing system 102 to perform policy underwriting (e.g., using underwriting systems 112) and/or claims processing (e.g., using claims processing systems 114). For example, as will be described further below, automobile insurance policyholders who suffer an accident and need to submit a claim on their policy may use their mobile device 500 to submit claim data to the insurance processing system 102 (e.g., to trigger a notice of loss or otherwise initiate claims processing). The data received by the insurance processing system 102 may be received via one or more application programming interfaces (APIs) 108 and routed to the claims processing systems 114 for processing. In some embodiments, the data may also be routed to the scoring engine 104 to update loss risk data (e.g., to provide data about the accident, the location and the nature of the claimed loss).

Pursuant to some embodiments, the API 108 may include one or more APIs that expose some or all of the scoring data to external services. For example, in one embodiment, an API may be provided that allows the scoring data to be merged or integrated with data from external mapping services, such as Google® Maps, or Mapquest®. In such embodiments, users viewing a map displayed on a mobile device 500, other user device 120 or vehicle device 122 may select to view an overlay or integrated display of risk data. Examples of such a view are provided and discussed further below in conjunction with FIG. 4. In this way, users may view, plan, and create routes designed to avoid or minimize their exposure to high loss risk areas.

Pursuant to some embodiments, data may be transmitted between devices using a wireless network. In some embodiments, some, or all, of the data may be transmitted using other network communication techniques (e.g., such as satellite communication, RFID, or the like). In some embodiments, some or all of the data transmitted between devices may be encrypted or otherwise secured to prevent intrusion.

Figure 2:
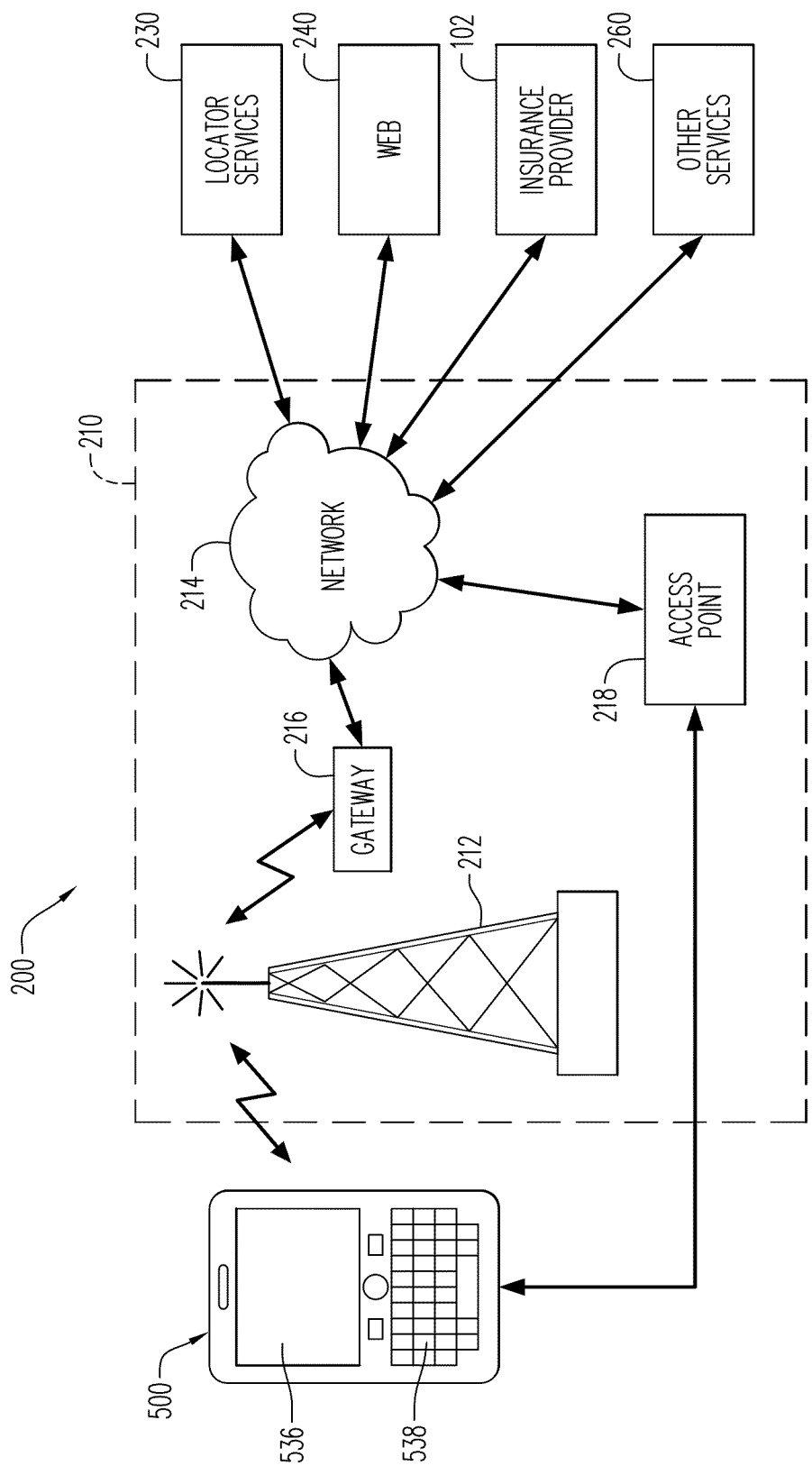
FIG. 2 illustrates a mobile system architecture within which some embodiments may be implemented.

Reference is now made to FIG. 2, which is a block diagram of an example network environment 200 showing communication paths between a mobile device 500 and the insurance processing systems 102 (as well as other devices and data sources). The mobile device 500 may be, for example, a mobile telephone, PDA, personal computer, or the like. For example, the mobile device 500 may be an iPhone® from Apple, Inc., a BlackBerry® from RIM, a mobile phone using the Google Android® operating system, or the like. In general, mobile device 500 may be any mobile computing and/or communications device which is capable of executing the insurance applications described below.

The mobile device 500 of FIG. 2 can, for example, communicate over one or more wired and/or wireless networks 210. As an example, a wireless network can be a cellular network (represented by a cell transmitter 212). A mobile device 500 may communicate over a cellular or other wireless network and through a gateway 216 may then communicate with a network 214 (e.g., such as the Internet or other public or private network). An access point, such as access point 218 may be provided to facilitate data and other communication access to network 214. The access point 218 may be, for example, compliant with the 802.11g (or other) communication standards.

In some embodiments, mobile device 500 may engage in both voice and data communications over the wireless network 212 via access point 218. For example, the mobile device 500 may be able to place or receive phone calls, send and receive emails, send and receive short message service ("SMS") messages, send and receive email messages, access electronic documents, send and receive streaming media, or the like, over the wireless network through the access point 218. Similar communications may be made via the network 212.

In some embodiments, a mobile device 500 may also establish communication by other means, such as, for example, wired connections with networks, peer-to-peer communication with other devices (e.g., using Bluetooth networking or the like), etc.

The mobile device 500 can, for example, communicate with one or more services over the networks 210, such as service providers 230-260 and the insurance processing systems 102 (described above in conjunction with FIG. 1). For example, a locator service 230 may provide navigation information, e.g., map information, location information, route information, and other information, to the mobile device 500.

Other services may include, for example, other web-based services 240 (e.g., such as data services or the like), media services (e.g., providing photo, video, music, or other rich content), download services (e.g., allowing applications and software or the like to be downloaded, etc.), and insurance services, such as the insurance services described further below (and including, for example, insurance reporting, customer service, underwriting, issuance, and the like).

The mobile device 500 can also access other data over the one or more wired and/or wireless networks 210. For example, content providers, such as news sites, RSS feeds, web sites, blogs, social networking sites, developer networks, etc., can be accessed by the mobile device 500. Such access can be provided by invocation of a web browsing function or application (e.g., a browser) in response to a user launching a Web browser application installed on the mobile device 500.

For example, in some embodiments described herein, the mobile device 500 may interact with insurance processing system 102 (of FIG. 1) to receive data associated with loss risk data generated by the scoring engine 104 (of FIG. 1) including the Loss Risk Scores by geocode, the Trip Risk Scores for routes, etc. The mobile device 500 may receive the loss risk data and integrate the data with a map (e.g., as shown and described below in conjunction with FIG. 4B) to allow route planning or driving to avoid high risk of loss areas (or "danger zones"). The mobile device 500 may also operate to transmit insurance-related data or driving data to the insurance processing system 102. For example, in a situation where the operator of the mobile device 500 is insured by the insurance company operating or associated with the insurance processing system 102, claim data associated with a collision, theft or other loss may be reported using the mobile device 500. An example of such a claims processing situation are provided below in conjunction with FIGS. 7 and 8. In some embodiments, an operator of the mobile device 500 may operate the mobile device 500 to submit traffic information, accident information or other information that may be relevant to other users, or to the collection of loss related data for use by the scoring engine 104. An example of such a submission is provided below in conjunction with FIG. 9. In still further embodiments, mobile device 500 (or vehicle devices 122) may be configured to collect and transmit vehicle or operator driving patterns for use in pricing, underwriting or otherwise administering insurance policies. An example of such an embodiment is provided below in conjunction with FIG. 10.

A number of pricing formulas may be used to incorporate the loss risk scores (described above) into a pricing determination. For example, in one illustrative embodiment, the following formula may be used:

$$\text{Price} = \text{Factor } A \times \text{Factor } B \times \text{Factor } C \times \text{Factor } D \times \text{Factor } E \times \text{Base Rate}$$

Where the Factor (x) is a number between 1.00 and 1.99 calculated from a formula using a defined set of Factor Inputs. The Factor Inputs are pre-defined rating variables from a table of different classifications. The Base Rate is a monetary number used for a unit of risk coverage (e.g., Base Rate for vehicles in State of New York or Base Rate for all private passenger vehicles in State of New York). The unit of risk coverage for a particular Base Rate could be for a broad set unit of time and place (year, state). Pursuant to some embodiments, as risk data may be received substantially in real time or on a regular basis, the unit of risk coverage for a particular Base Rate could be much more granular thanks to the dynamically changing data. For example, the unit of risk coverage could be expressed as a base rate per minute, and/or a base rate per mile, or base rate per geocode. As another example, the data may be used to perform "pay as you go" pricing of policies. As an example, in some embodiments, pay as you go, or route or trip specific pricing may be provided and communicated to a user pursuant to some embodiments. A driver on a pay as you go plan may request several different route options and receive pricing for each of the routes so that the driver can pick a desired route based on price, time, and other factors.

In the example pricing formula shown above, a number of Factor Inputs may be used, including, for example, those shown in the Table 1 below.

TABLE 1

| Factor Inputs | Type of Factor |
| --- | --- |
| Person Risk Score (based on Trip Risk Score) | E (non traditional) |
| Vehicle Risk Score (based on Trip Risk Score) | E (non traditional) |
| Credit Score (where legally available) | A |
| Age | A |
| # of at fault accidents | A |
| # of not at fault accidents | A |
| # of accident violations | A |
| # of passenger vehicles owned | A |
| Have prior insurance | B |
| Months since last auto accident | B |
| Months since last comprehensive loss on policy | B |
| Annual Mileage | B |
| Years with Insurance Firm | B |
| Years of owning residence | B |
| Years with clean driving record | B |
| Marital Status | C |
| Gender | C |
| Vehicle Age | C |
| Annual Mileage | C |
| Vehicle Use | C |
| Safe Driver Program | C |
| Non resident student | D |
| Air Bag Safety Discount | D |
| Anti Theft Device | D |
| Mature operator vehicle safety course | D |
| Own hybrid vehicle | D |
| Registered Mobile GPS device | D |

These pricing factors, as well as the risk scoring criteria discussed herein, are provided for illustrative purposes. The factors and criteria used in conjunction with any given insurer or product will be selected and used in a manner that is in conformance with any applicable laws and regulations. Pursuant to some embodiments, more granular pricing may be achieved by using several "non-traditional" pricing factors, including the Person Risk Score, the Vehicle Risk Score and the Trip Risk Score generated by the scoring engine of the present invention. Further, because the data may be obtained based on actual usage patterns obtained from mobile device 500 (or from vehicle devices, in some embodiments), the pricing may accurately reflect the actual loss risk associated with the usage patterns of a particular driver or vehicle.

The mobile device 500 can perform a number of different device functions. For example, the mobile device 500 may operate as a telephone, an email device, a network communication device, a media player device, etc., under control of one or more applications installed on the mobile device 500. In some embodiments, a user operating the mobile device 500 may interact with the applications using a keypad 538 which may be a tactile keypad with individual keys, or which may be a touch screen keypad. The user is presented with information and graphics on a display screen 536.

Figure 3A:
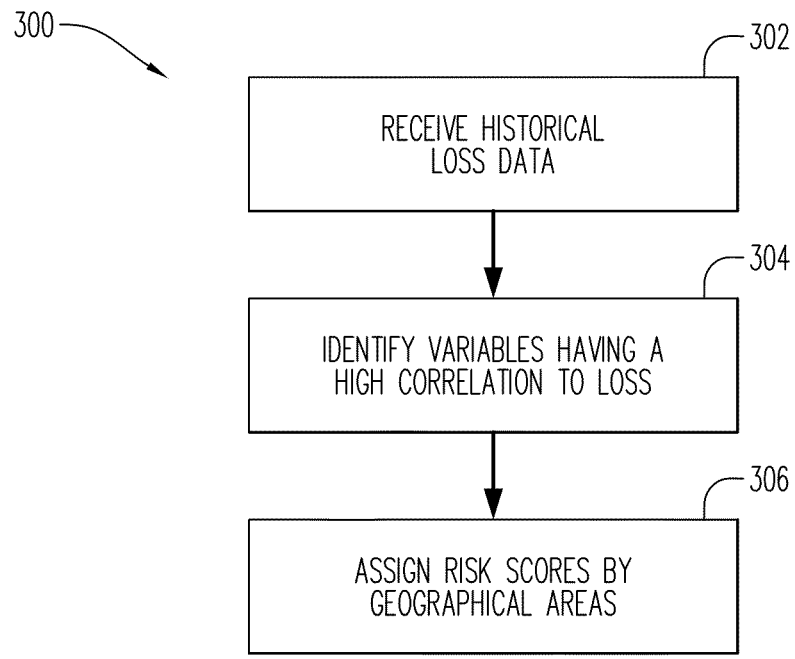
FIGS. 3A and 3B are flow diagrams depicting processes for creating and updating scores pursuant to some embodiments.
Figure 3B:
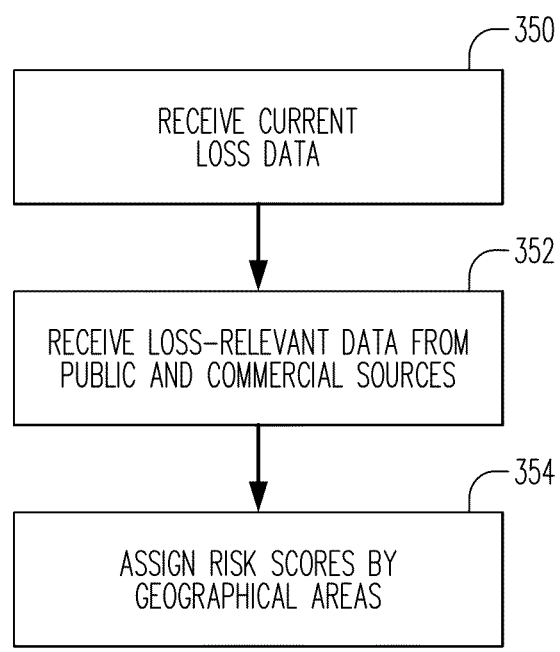

Reference is now made to FIGS. 3A and 3B where flow diagrams are shown which depict processes 300 that may be performed by the insurance processing system 102 of FIG. 1 to generate loss risk scores using the scoring engine 104. Referring first to FIG. 3A, a process 300 may be performed to generate loss risk scores (including the Loss Risk Scores, the Trip Risk Scores, and/or the Vehicle or Person Risk Scores described above) that may be used in insurance processing. The process 300 may be performed on an as needed basis to assign loss risk scores to geographical regions (e.g., such as ZIP code areas, ZIP+5 areas, or more granular areas based on latitude and longitude). Processing begins at 302 where historical loss data are received for processing. Historical loss data may be obtained from a data source such as historical loss database 106 of FIG. 1. In some embodiments, the historical loss data may be data associated with a single insurer. For example, in situations where the system 100 is operated by or on behalf of a particular insurer, the historical loss data may be loss data accumulated by that insurer. In some embodiments, a group, association or affiliation of insurers may aggregate historical loss data to provide a more accurate loss risk score. In such embodiments, the data received at 302 may include receiving data from one or more third party sources (e.g., such as commercial data sources 118). In some embodiments, processing at 302 may include pre-processing or formatting the data to a desired input format. Such processing may also include geocoding the data to a preferred format (e.g., such as using KML or other geographic formatting of data).

Processing continues at 304 where the system is operated to identify one or more variables having a high correlation to loss. For example, some variables may clearly have a high correlation to loss, such as theft, collision, or the like. Other variables may be identified based on analysis at 304. Processing continues at 306 where risk scores are generated and assigned to individual geographical areas or regions. For example, as the risk scores are calculated based on location, scores may be assigned to specific areas (such as by ZIP code or the like) so that those areas may be assigned a relative loss risk score (e.g., such as by using the Loss Risk Score formula described above by geocode).

Reference is now made to FIG. 3B, where a further flow diagram is shown. The flow diagram of FIG. 3B depicts a process for updating loss risk scores based on current or additional information received from various sources (such as public data sources 116, commercial data sources 118, mobile devices 500, user devices 120 and vehicle devices 122). Processing begins at 350 where current loss data is received. For example, current loss data may include new loss claim data received from an insurance policy holder who has submitted a claim using his or her mobile device 500 (as described below in conjunction with FIG. 11), or accident event information received from a user operating a mobile device 500 (as described below in conjunction with FIG. 7). The data received at 350 may be geocoded and formatted so that existing loss risk data and scoring may be updated.

Processing continues at 352 where loss-relevant data from public or commercial sources are received. The loss-relevant data may be information not directly associated with a loss but that is relevant to assessing the likelihood or risk of loss in different geographical areas. For example, data received at 352 may include traffic event information received from a user operating a mobile device 500 (as described below in conjunction with FIG. 9). Other data received at 352 may include police report data (from public data sources 116), or theft report data (from public data sources 116 and/or commercial data sources 118). The data received at 352 may be geocoded and formatted so that existing risk data and scoring may be updated.

Processing continues at 354 where the scoring engine 104 operates to assign updated risk scores by geographical area based on the new or updated information received at 350 and 352. The data updated by the processes of FIG. 3 may be provided to users in a number of different ways. For example, referring now to FIG. 4A, a diagram 400 depicting a user interface 402 is shown. The user interface 402 may be displayed on a computer, on a mobile device (such as the device 500 of FIG. 1), or on any type of display device that can receive data from insurance processing system 102.

The user interface 402 depicts a portion of a map showing a portion of Fairfield County in the State of Connecticut.

More particularly, the map shows ZIP code regions of Fairfield County with certain ZIP code regions (such as regions 404-408) having different shading or hatching. The shading or hatching depicts the relative loss risk suffered by drivers in each ZIP code region, with certain rural ZIP code regions (shown without shading or hatching, such as region 404) having a lower risk than other ZIP code regions (such as region 406 with a high loss risk, and region 408 with a moderate loss risk).

The regions and their relative loss risk scores are purely illustrative and are used for purposes of describing features of some embodiments of the present invention. However, pursuant to some embodiments, entire coverage areas may be scored or have their relative risk assessed. Scores or risk levels may be depicted in a number of different ways, including using color codes (e.g., such as red for high risk, yellow for moderate risk, and green for low risk), hatching, numeric scores, or the like. In some embodiments, the presentation of risk levels may be used to primarily to communicate specific "danger zones" to drivers or vehicle operators. Pursuant to some embodiments, the scoring and geocoding of data may be performed on an ongoing basis, with updates performed substantially in real time. As a result, large accidents, disasters, weather conditions, time of day, traffic patterns, and other events may cause the scoring to change, and the presentation of such changes to users operating mobile devices 500 or other devices allows such users to react to or take steps to avoid any danger zones or areas of higher than normal risk.

Figure 4A:
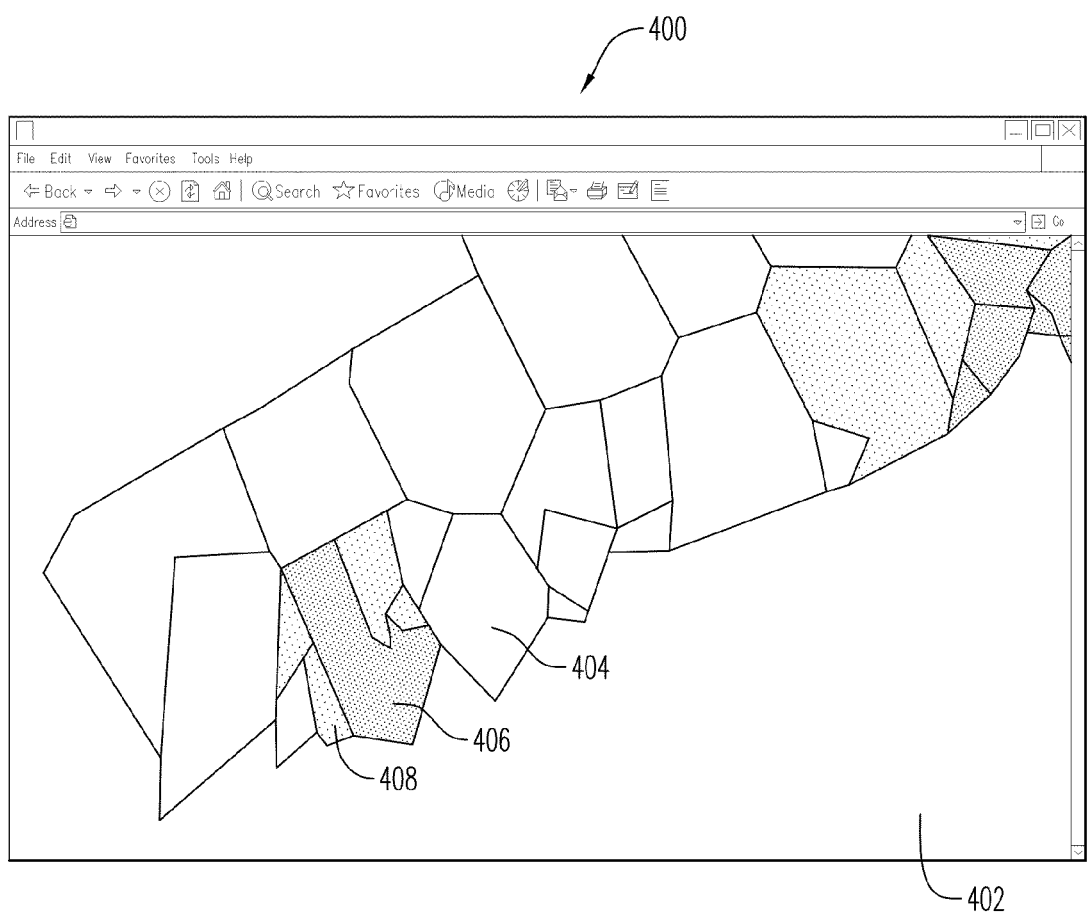
FIGS. 4A and 4B are block diagrams depicting user interfaces pursuant to some embodiments.
Figure 4B:
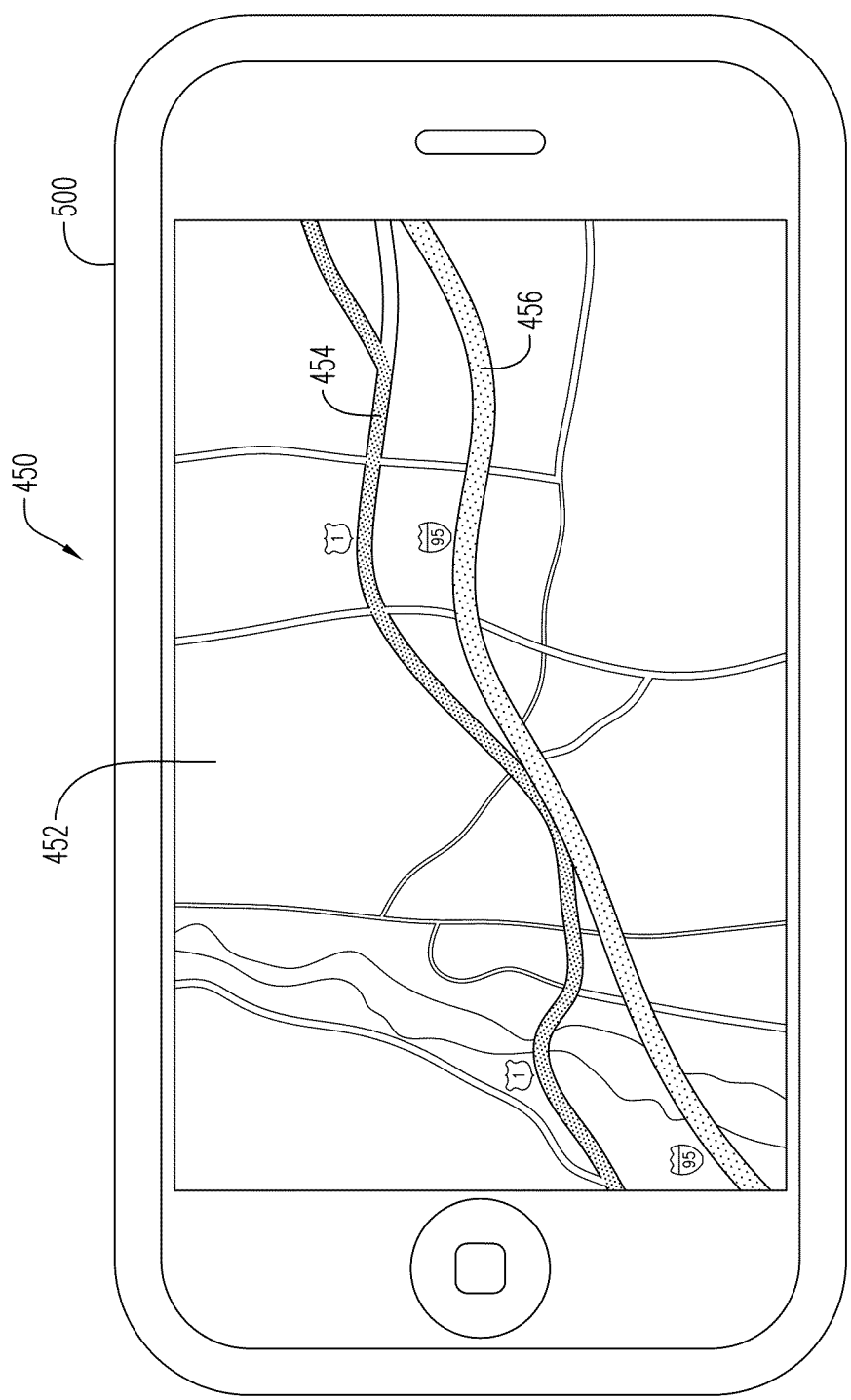

In some embodiments, such as the one depicted in FIG. 4B, users operating devices such as a mobile device 500, may access risk score information in order to identify a safe route or to assess the relative risk associated with multiple route options. For example, Trip Risk Score maybe generated for each of the multiple route options. As shown in FIG. 4B, a user is viewing a portion of a route map. In the illustrative interface, the user is viewing a route through Fairfield County Connecticut, and has two route choices—a surface street (shown as Route "1") or a freeway (shown as Interstate "95"). The relative level of loss risk posed between the two routes is depicted by shading or coloring. In the illustrative example, the choice of Route 1 (shown as item 454) is shaded darker than the alternative route (shown as item 456). The darker shading may indicate that the surface street (which traverses a downtown area with multiple traffic issues and intersections) has a higher risk of loss than the alternative route. In this manner, users operating mobile devices 500 (or other devices, such as vehicle navigation systems or computers), may proactively choose to take routes that have lower risk of vehicle damage, passenger injury, or other losses.

Similar maps may be generated for specific loss risks. For example, a user may wish to find the relative danger of parking in one parking lot over another parking lot. Embodiments allow users to request specific loss risk score and receive the data in a visual representation such as a map or a map overlay. Other route planning, mapping, and graphical uses of such risk data will be described further below in conjunction with FIG. 9.

Figure 5:
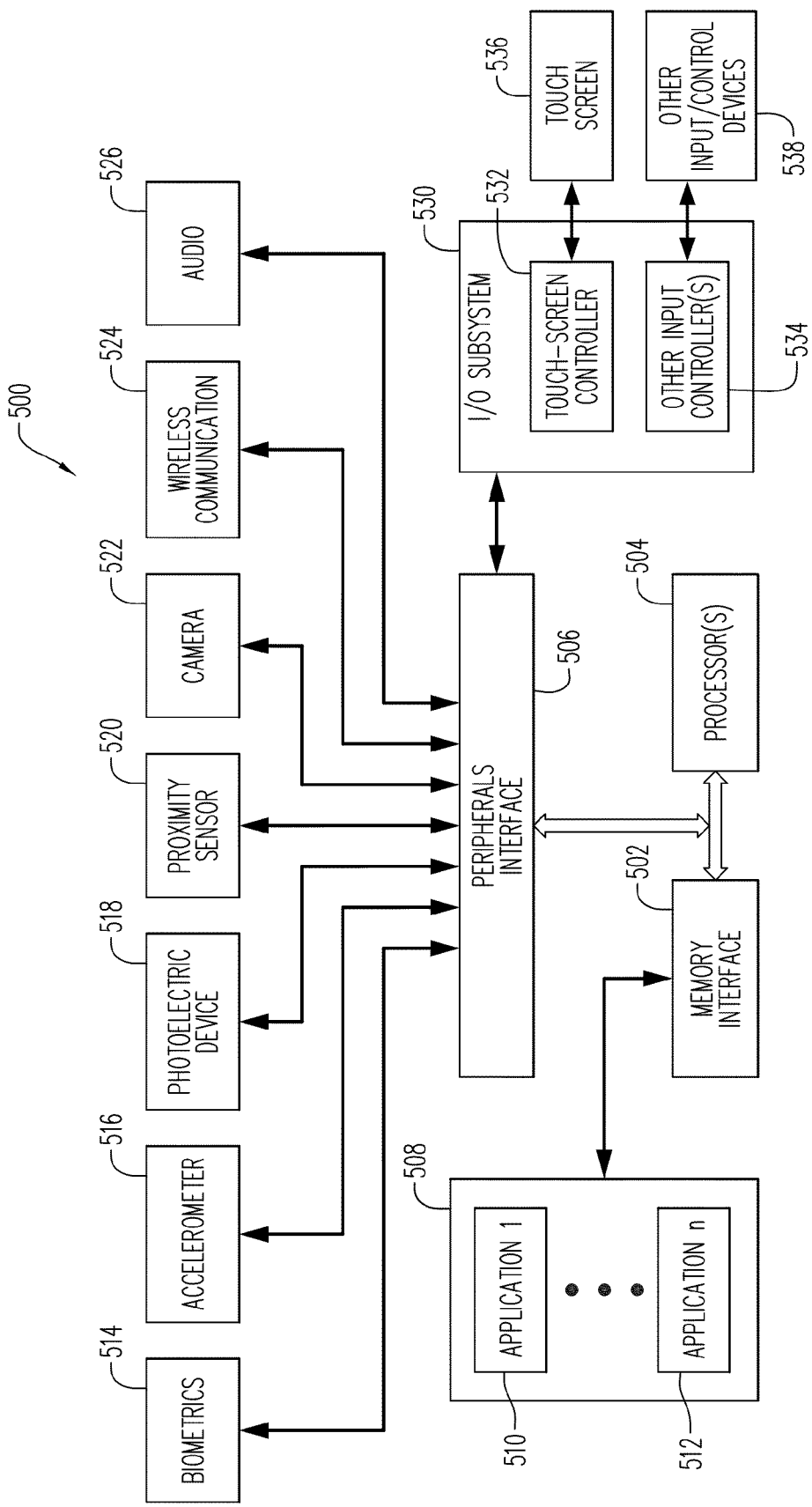
FIG. 5 is a partial functional block diagram of a mobile device and system provided in accordance with some embodiments.

Reference is now made to FIG. 5, where details of a mobile device 500 according to some embodiments is shown. As depicted, the mobile device 500 includes a number of components which may be controlled or perform functions in conjunction with one more application programs 510-512 to perform the features of some embodiments.

The mobile device 500 can include a memory interface 502 one or more data processors, image processors and/or central processing units 504, and a peripherals interface 506. The memory interface 502, the one or more processors 504 and/or the peripherals interface 506 can be separate components or can be integrated in one or more integrated circuits. The various components in the mobile device 500 can be coupled by one or more communication buses or signal lines.

Sensors, devices and subsystems can be coupled to the peripherals interface 506 to facilitate multiple functionalities. For example, a biometrics sensor 514, an accelerometer 516, a photoelectric device 516, a proximity sensor 520, a camera 522, a wireless communication unit 524, and an audio unit 526 may be provided to facilitate the collection, use and interaction with data and information and to achieve the functions of the insurance applications described further below.

The mobile device 500 may include one or more input/output (I/O) devices and/or sensor devices. For example, input controllers 534 may be provided with a speaker and a microphone (not shown) to facilitate voice-enabled functionalities, such as phone and voice mail functions. In some implementations, a loud speaker can be included to facilitate hands-free voice functionalities, such as speaker phone functions. An audio jack can also be included for use of headphones and/or a microphone.

The I/O subsystem 530 can include a touch screen controller 532 and/or other input controller(s) 534. The touch-screen controller 532 can be coupled to a touch screen 536. The touch screen 536 and touch screen controller 532 can, for example, detect contact and movement or break thereof using any of a plurality of touch sensitivity technologies, including but not limited to capacitive, resistive, infrared, and surface acoustic wave technologies, as well as other proximity sensor arrays or other elements for determining one or more points of contact with the touch screen 536.

The other input controller(s) 534 can be coupled to other input/control devices 538, such as one or more buttons, rocker switches, thumb-wheel, infrared port, USB port, and/or a pointer device such as a stylus. The one or more buttons (not shown) can include an up/down button for volume control of the speaker and/or the microphone.

In some implementations, a proximity sensor 520 can be included to facilitate the detection of the user positioning the mobile device 500 proximate to the user's ear and, in response, to disengage the touch-screen display 536 to prevent accidental function invocations. In some implementations, the touch-screen display 536 can be turned off to conserve additional power when the mobile device 500 is proximate to the user's ear.

Other sensors can also be used. For example, in some implementations, a photoelectric device 518 may be provided to facilitate adjusting the brightness of the touch-screen display 538. In some implementations, an accelerometer 516 can be utilized to detect movement of the mobile device 500. In some embodiments, the mobile device 500 may include circuitry and sensors for supporting a location determining capability, such as that provided by the global positioning system (GPS) or other positioning system (e.g., systems using Wi-Fi access points, television signals, cellular grids, Uniform Resource Locators (URLs)). In some implementations, a positioning system (e.g., a GPS receiver) can be integrated into the mobile device 500 or provided as a separate device that can be coupled to the mobile device 500 through a peripherals interface 506 to provide access to location-based services. The positioning and location-based services may be used, for example, to tag data transmitted from the mobile device 500 to insurance provider systems 102 (e.g., in conjunction with the reporting of traffic, accidents, or filing claims, as will be described further below).

The mobile device 500 can also include a camera lens and sensor 520. In some implementations, the camera lens and sensor 520 can be located on the back surface of the mobile device 500. The camera can capture still images and/or video. The camera may be used, for example, to capture images of traffic incidents, vehicle collisions, or the like as will be described further below.

The mobile device 500 can also include one or more wireless communication subsystems 524, such as an 802.11b/g communication device, and/or a Bluetooth® communication device. Other communication protocols can also be supported, including other 802.x communication protocols (e.g., WiMax, Wi-Fi), code division multiple access (CDMA), global system for mobile communications (GSM), Enhanced Data GSM Environment (EDGE), 3G (e.g., EV-DO, UMTS, HSDPA), etc.

In some implementations, additional sensors or subsystems may be coupled to the peripherals interface 506 via connectors such as, for example a Universal Serial Bus (USB) port, or a docking port, or some other wired port connection.

The memory interface 502 can be coupled to memory 508. The memory 508 can include high-speed random access memory and/or non-volatile memory, such as one or more magnetic disk storage devices, one or more optical storage devices, and/or flash memory (e.g., NAND, NOR). The memory 508 can store an operating system, such as Darwin, RTXC, LINUX, UNIX, OS X, WINDOWS, or an embedded operating system such as VxWorks. The operating system may include instructions for handling basic system services and for performing hardware dependent tasks. In some implementations, the operating system can be a kernel (e.g., UNIX kernel).

The memory 508 may also store application programs 510-512 which act, in conjunction with the processors 504, to cause the mobile device to operate to perform certain functions, including the insurance related functions described further below.

The memory 508 can also store data, including but not limited to documents, images, video files, audio files, and other data. In some implementations, the memory 508 stores address book data, which can include contact information (e.g., address, phone number, etc.) for one or more persons, organizations, services, or entities. For example, in some embodiments, the memory stores insurance policy numbers or other unique identifiers to allow a user of the mobile device 500 to quickly access insurance policy related data and information.

In some embodiments, the mobile device 500 includes a positioning system. In some embodiments, the positioning system can be provided by a separate device coupled to the mobile device 500, or can be provided internal to the mobile device. In some implementations, the positioning system can employ positioning technology including a GPS, a cellular grid, URIs or any other technology for determining the geographic location of a device. In some implementations, the positioning system can employ a service provided by a third party or external positioning. In other implementations, the positioning system can be provided by an accelerometer and a compass using dead reckoning techniques. In such implementations, the user can occasionally reset the positioning system by marking the mobile device's presence at a known location (e.g., a landmark or intersection). In still other implementations, the user can enter a set of position coordinates (e.g., latitude, longitude) for the mobile device. For example, the position coordinates can be typed into the phone (e.g., using a virtual keyboard) or selected by touching a point on a map. Position coordinates can also be acquired from another device (e.g., a car navigation system) by syncing or linking with the other device. In other implementations, the positioning system can be provided by using wireless signal strength and one or more locations of known wireless signal sources to provide the current location. Wireless signal sources can include access points and/or cellular towers. Other techniques to determine a current location of the mobile device 500 can be used and other configurations of the positioning system are possible.

Figure 6:
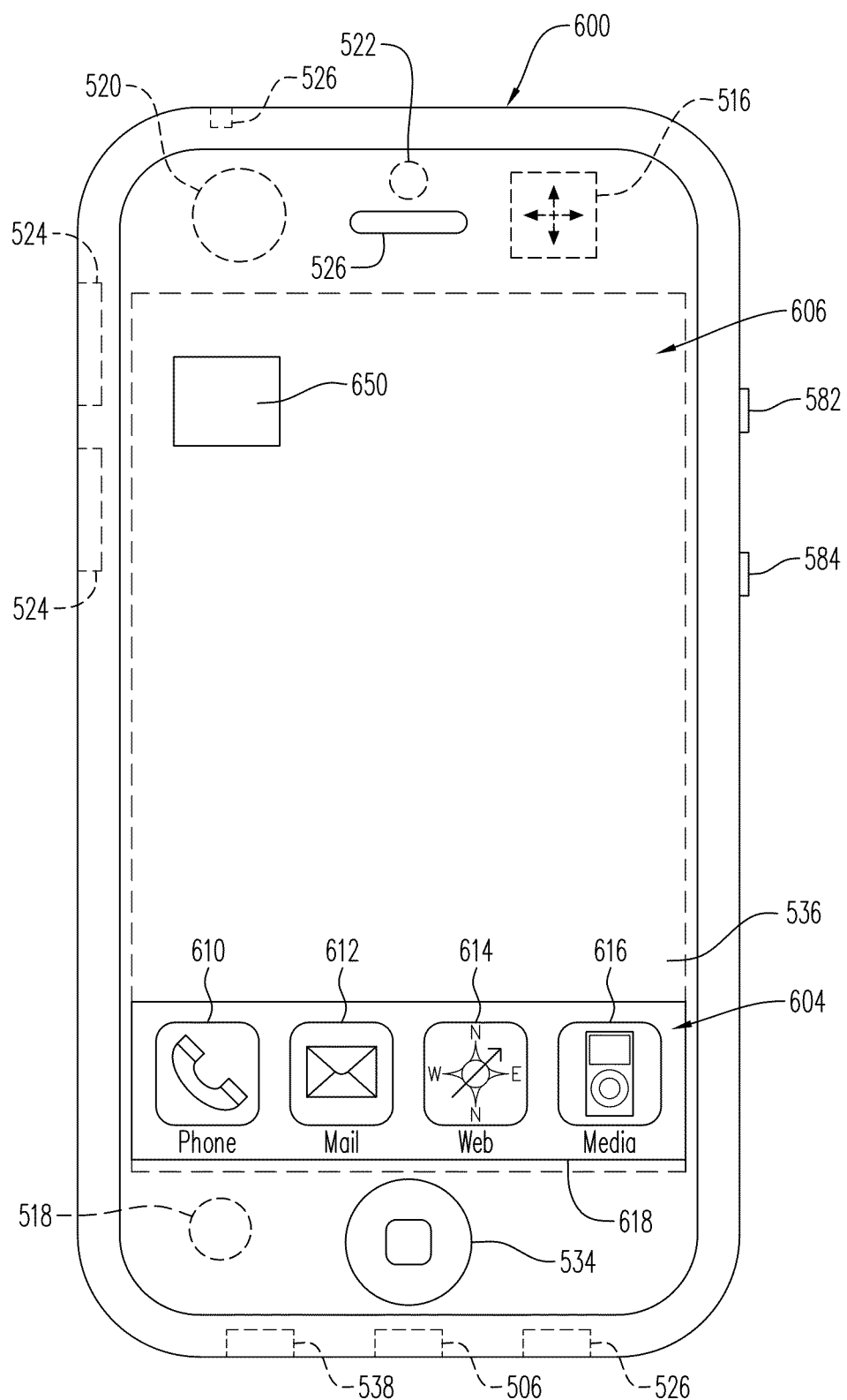
FIG. 6 is a block diagram of the mobile device of FIG. 5.

Reference is now made to FIG. 6, where a mobile device 500 is shown. As shown, the mobile device 500 can launch (and operate under the control of) one or more application programs by selecting an icon associated with an application program. As depicted, the mobile device 500 has several application programs (and corresponding icons), including an insurance application (launched by selecting icon 650), a phone application (launched by selecting icon 610), an email program (launched by selecting icon 612), a Web browser application (launched by selecting icon 614), and a media player application (launched by selecting icon 604). Those skilled in the art will recognize that mobile device 500 may have a number of different icons and applications, and that applications may be launched in other manners as well (e.g., using hot keys, drop down selectors, or the like). In the embodiment shown, an application, such as the insurance application, is launched by the user tapping or touching an icon displayed on the touch screen 536 interface of the mobile device 500.

Once an application is launched, the user may interact with the application, and the mobile device may function pursuant to the program instructions associated with the application. In the various insurance applications described further below, details of some operation of the mobile device 500 will be described.

Pursuant to some embodiments, an application may be stored in, or accessible to, memory 508 of mobile device 500 which allows a user of mobile device 500 to participate in insurance or claim related "crowdsourcing" of data. For example, in some embodiments, the insurance application may allow user-initiated reporting of accidents or events. In some embodiments, a user operating a mobile device 500 may launch the application and select an option such as "report an incident". The option may provide a selection of different types of incidents (e.g., such as an automobile accident, a personal injury, a fire, a robbery, a natural disaster, etc.) and may prompt the user for additional information. Data from the mobile device, including a user identifier, a location of the user, and the user provided data are transmitted over a network to an insurance service provider 102 for collating the data. In some embodiments, a user may provide commentary (e.g., by entering a textual description of the event, by recording a voice narrative, by taking one or more still photos, by taking one or more video recordings, etc.) of the event. Such commentary will be transmitted over a network to the insurance system 102. In some embodiments, the data received by the insurance system 102 is used to update, modify or otherwise maintain accurate and current information for use by scoring engine 104.

In some embodiments, a map of events near a user's location may also be presented and users in the area of an event may be prompted to provide further data about the event. In this manner, for example, a number of separate users may provide near real-time evidence or documentation about events that may trigger insurance coverage so that the insurer may more accurately process claims arising from the event. For example, in some embodiments, when users operating mobile devices 500 transmit information to insurance system 102, the mobile device 500 tags the data with the user's geocoded location and a timestamp.

In some embodiments, users may be provided with an incentive for submitting such event data. For example, users who are insured or might become insured by an insurance company operating the service may receive a benefit (e.g., such as a discount or coupon) based on the number, quality and type of events the user provides data about.

In some embodiments, the data from such user reported events may be presented on a map or other user interface that is transmitted from the insurance system 102 to individual mobile devices 500. The data may then be used to alert users about nearby events so that the user can adjust their location accordingly (e.g., to avoid a traffic accident, to depart from an area with a natural disaster, etc.). In some embodiments, the insurance service provider may use such event data to transmit alerts or notifications to individual users in the area of an event.

In the event of catastrophes or natural disasters (e.g., such as tornados, floods, terrorist activities, etc), user data may be collected substantially in real-time to monitor the extent and exact location of such events and to alert other users of the location and extent of such events.

Figure 7:
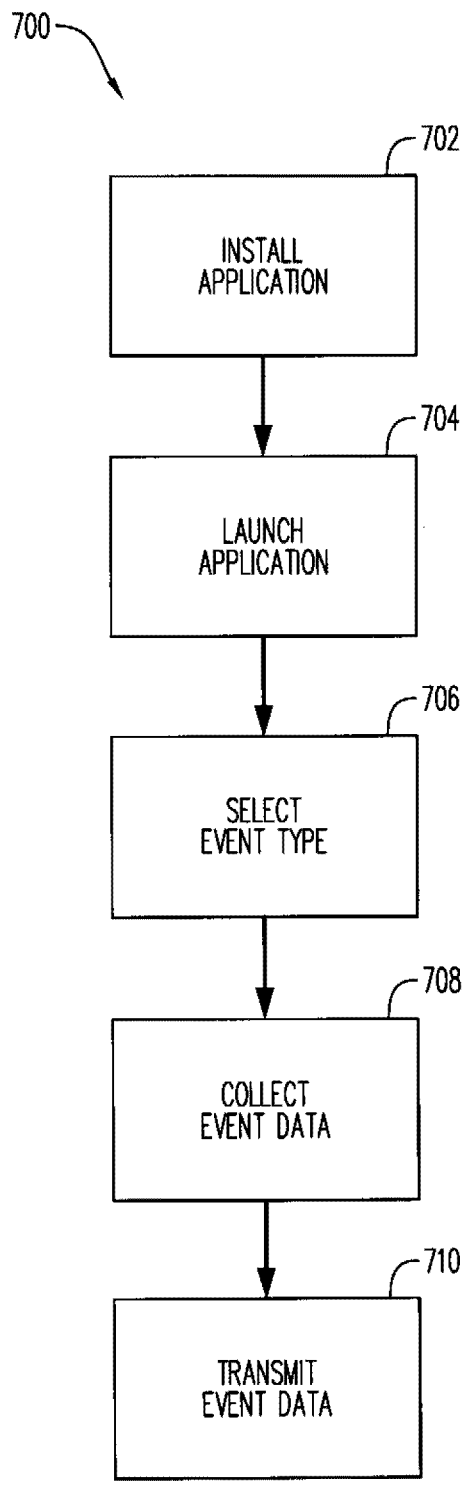
FIG. 7 is a flow diagram depicting a process for collecting and presenting data from a plurality of users operating devices such as the device of FIG. 5 pursuant to some embodiments.

Reference is now made to FIG. 7, which shows a process 700 for installing and using an application pursuant to some embodiments. Process 700 may be performed using a mobile device such as the mobile device 500 described above. As shown, processing begins at 702 where a user of a mobile device 500 downloads and installs the insurance application. This download and install may be performed from the mobile device 500 or from a desktop computer in communication with the mobile device 500. The application may be downloaded from the insurance system 102 or from an application marketplace.

Processing continues at 704 where a user launches the application, e.g., to report on an event witnessed by the user. Processing continues at 706 where the user selects or designates a type of event he or she wishes to report on (e.g., such as a flood, an accident, a fire, or the like). Processing continues at 708 where the user manipulates the mobile device 500 to collect event data. For example, processing at 708 may include the user taking a photo or a video of the event scene, and/or providing a textual or voice recorded description of the event. Processing continues at 710 where the event data is transmitted to an insurance system 102 for further processing. In some embodiments, the application causes geolocation data to be appended to or otherwise associated with the event data. The event data and the geolocation data are then manipulated by the insurance system 102 to provide information to other users or to amass details about the event. In some embodiments, the data may be used in conjunction with insurance processing such as the insurance processing described further below in conjunction with FIGS. 13-19.

Pursuant to some embodiments, an application may be stored in, or accessible to, memory 508 of mobile device 500 which allows a user of mobile device 500 to participate in insurance or claim related reporting of data. For example, a user who has installed an insurance application of the present invention on a mobile device 500 and who witnesses an event may collect, annotate, and transmit the event data to an insurance system 102 via a network interface. As a specific example, where a user witnesses (or is a participant in) a traffic accident involving multiple parties (e.g., such as where the user is a rider on a bus during a bus accident), the user may launch an insurance application and collect, annotate and transmit information associated with the accident to an insurance system 102. One common problem in such events is the processing of claims by parties who purport to have been present in the event, but whose presence cannot be verified. Using features of the present invention, witnesses who were actually present at the scene of the event can record scenes from the event, including pictures and videos of the participants in the event. This data can be time stamped, geocoded and verified as coming from the scene of the event, and can later be used by the insurance 102 to authenticate and process claims arising from the event.

In some embodiments, users who submit such data to the insurance system 102 may receive benefits such as discounts in policies or the like. Further, users who suffered injury from such events may enjoy faster claim processing, as additional paperwork may be minimized and delays associated with claim processing may be reduced.

Similar features may be used in insurance applications which are used to report, record and prove damage from single vehicle or other accidents. For example, a user who is an insured who suffers a single-car accident may use the application to document the extent of damages suffered in the accident. The data transmitted to the insurance system 102 may include geocoded location information as well as time and date information to document the location and time of the event. Such data may be used in conjunction with official accident reports to verify the insured's claim.

Figure 8:
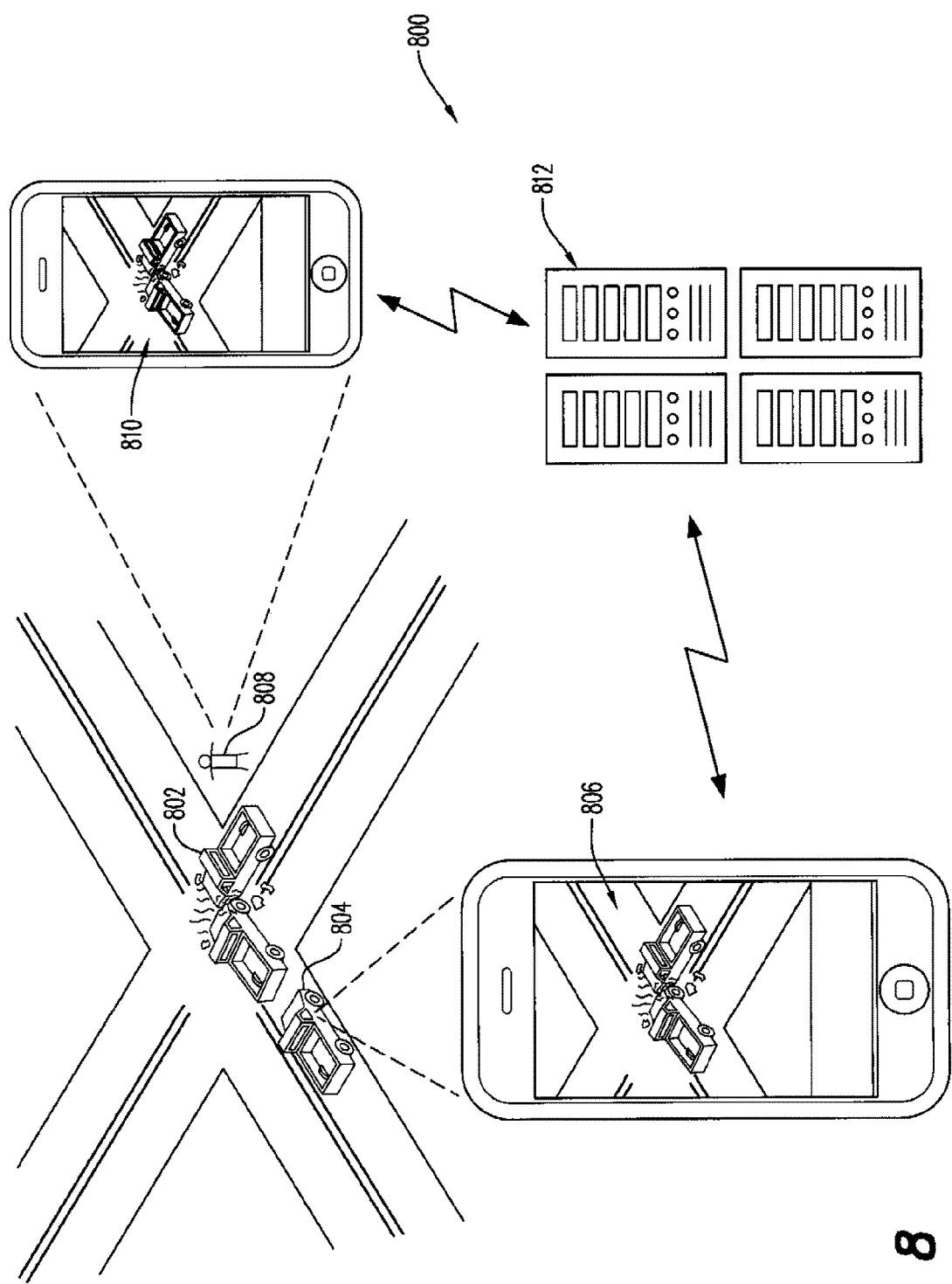
FIG. 8 is a block diagram depicting an accident verification system pursuant to some embodiments.

Reference is now made to FIG. 8 where one embodiment of an accident verification system 800 is shown. As depicted, the accident verification system 800 includes a number of components interacting to allow users of mobile devices 806 and 810 to operate an accident verification application to capture accident or event details. In the system of FIG. 8, two users of mobile devices 500 have installed an accident verification application pursuant to the present invention and are at the scene of a car accident (and may be the insured of one of the vehicles in the accident). One user 808 is standing near the scene and captures one view of the accident by taking a photo or video from her perspective of the accident. The image (and other details, including geocoded data) are transmitted to an insurance system 812 for further processing. Another operator 804 is a passenger in a vehicle just behind the scene and captures a second view of the accident by taking a photo or vide from his perspective of the accident. Again, the data is transmitted to the insurance system 812 for processing.

The insurance system 812 may use the data to verify details of the accident, process claims, or otherwise handle claims arising from the accident. Further examples of some embodiments of such claim or accident reporting using a mobile device 500 are provided below in conjunction with a description of FIG. 12.

Pursuant to some embodiments, an application may be stored in, or accessible to, memory 508 of mobile device 500 which allows a user of mobile device 500 to download and install an application which may be used to alert or notify the user of dangerous areas or areas which have higher than normal risks of accidents or injury. In some embodiments, the application installed on the mobile device 500 interacts with data from an insurance system 102 over a network interface (such as the network of FIG. 2). As a user moves around (e.g., by driving in a car, or by walking, etc.), the application sends updates of the user's location to the insurance system 102. The insurance system 102 uses the location data to compare the user's location (and, for example, the user's trajectory or path) to identify nearby areas that have higher than average accident or injury claims (as scored by the scoring engine 104 of FIG. 1). This accident and injury data may be generated by map snapping or by geocoding historical accident and injury data as described above in conjunction with FIG. 1.

If the user's trajectory or path is likely to take the user to an area of high risk, a notice or warning may be provided. For example, a voice prompt may be generated if the user is driving toward an intersection that has a very high number of accidents stating "Careful, the intersection of Oak and Main is dangerous, please use caution when going through the intersection." Other types of notifications may also be provided (and may, in some embodiments, be configured or specified by the user).

In some embodiments, the application may be used to construct a route plan, with a risk rating for each of several alternative routes so that a user may select the lower-risk of alternative routes (e.g., as shown in the illustrative map of FIG. 4B). In some embodiments, a route risk score may be generated allowing the user to select the more desirable route.

Figure 9:
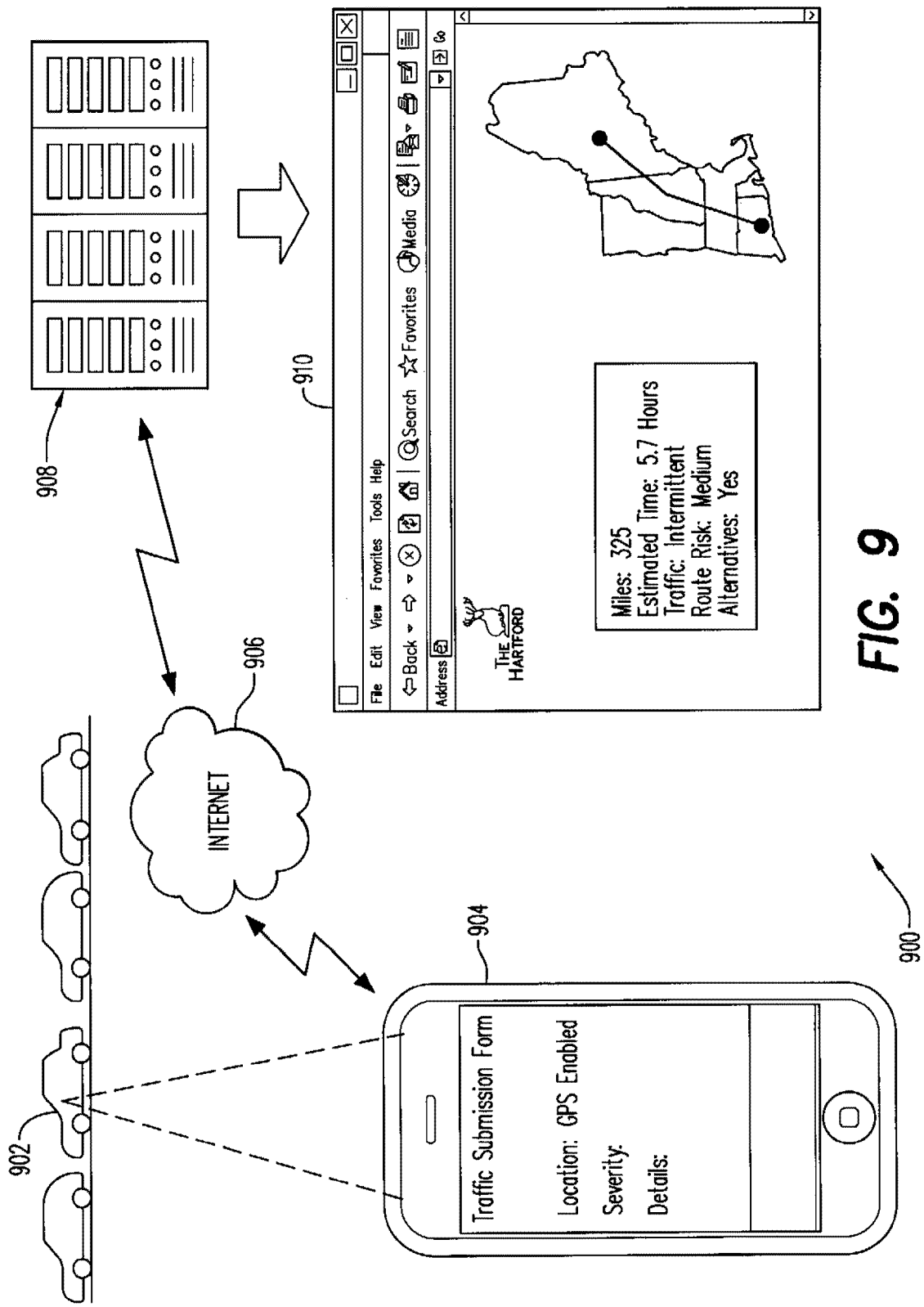
FIG. 9 is a block diagram depicting a route selection system pursuant to some embodiments.

Reference is now made to FIG. 9 where a system 900 is shown in which a user 902 is operating a mobile device 904 on which an insurance application pursuant to the present invention is installed. The user 902 is the operator or a passenger in a vehicle stuck in a traffic jam and operates the application to submit details of the traffic situation (including a geolocation of the traffic jam and a severity of the jam as well as other relevant details). The information is transmitted from the mobile device 904 to an insurance or other processing system 908 via a network 906. The processing system 908 aggregates data from a plurality of different users to create a report of the danger area or traffic situation that can be viewed (or otherwise received) by other users.

Pursuant to some embodiments, an application may be stored in, or accessible to, memory 508 of mobile device 500 which allows a user of mobile device 500 to track a user's driving patterns to provide insurance coverage and pricing based on the user's actual behavior. For example, currently, a driver in Kansas who claims to drive 10,000 miles a year will pay less for insurance than a similarly-aged driver in New York City who also claims to drive 10,000 miles a year. However, it may turn out that the driver in Kansas should pay more if the driver engages in higher risk driving patterns than the New York driver. Pursuant to some embodiments, drivers may download an application and install it on their mobile device 500 so that their driving patterns may be tracked or monitored. In some embodiments, drivers who participate may receive premium discounts or other incentives to participate.

Pursuant to some embodiments, a driver who has downloaded and installed the insurance application on a mobile device 500 will be prompted to register the application with the insurer. Once registered, in some embodiments, the mobile device 500 may be configured to recognize when the driver is in his or her insured vehicle (e.g., by synching with a blue tooth device of the car, by scanning a bar code, RFID code, or other tag associated with the vehicle, etc.). Once registered and configured, the driver may use the mobile device 500 to track his or her driving patterns. In some embodiments, a weekly or monthly sample may be taken to track how and where the driver operates the vehicle to determine if insurance coverage can be granted or modified.

In this manner, operators may qualify for improved insurance terms and insurers may more appropriately cover insureds.

Figure 10:
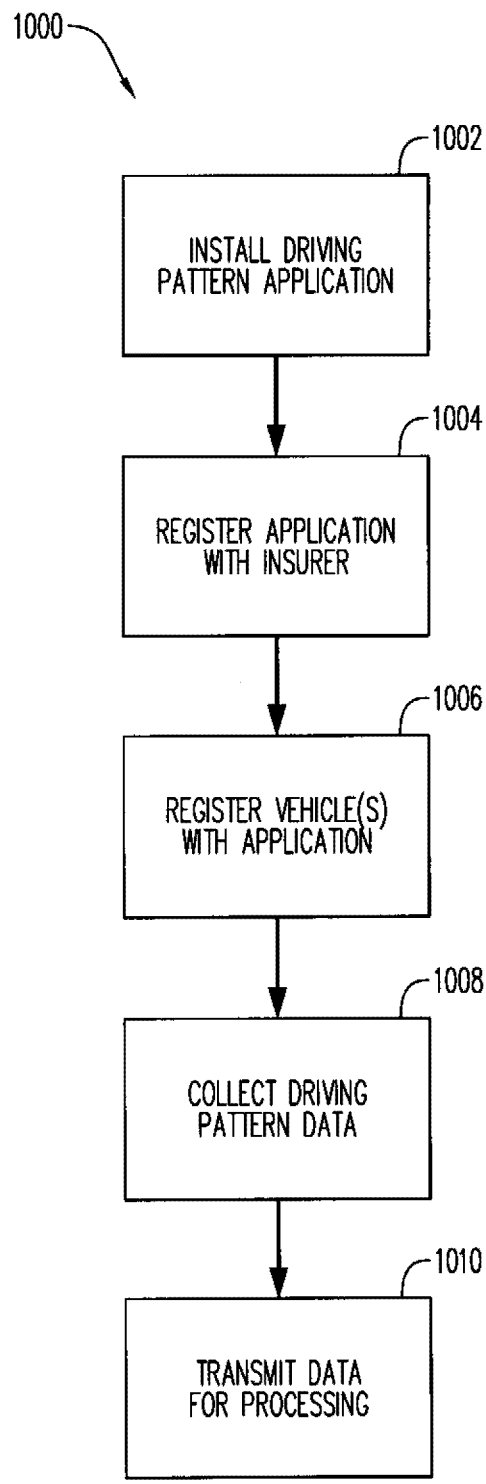
FIG. 10 is a flow diagram depicting a process for collecting and processing driving pattern data pursuant to some embodiments.

Reference is now made to FIG. 10 where a process 1000 is shown for installing and using a driving pattern application pursuant to some embodiments. Process 1000 may be performed using a mobile device such as the mobile device 500 described above. As shown, processing begins at 1002 where a user of a mobile device 500 downloads and installs the driving pattern application. This download and install may be performed from the mobile device 500 or from a desktop computer in communication with the mobile device 500. The application may be downloaded from the insurance processing system 102 or from an application marketplace. In some embodiments, the application may be installed at the request of an insurer, or as an option provided by an insurer so the user may qualify for reduced rates or as part of an underwriting process performed by an insurer.

Processing continues at 1004 where the user interacts with the application to register the application with their insurer (e.g., by providing a policy number or the like). Processing continue at 1006 where the vehicle(s) to be monitored are registered with the application (e.g., by synching the application and the mobile device with a bluetooth system of the vehicle, by reading an RFID tag installed in the vehicle or the like).

Processing continues at 1008 where the application is operated to collect driving pattern data. The application may be triggered once the vehicle moves or when activated by the user. Location data may be collected while the vehicle is in operation to track data such as a vehicle's route, speed, driving characteristics, or the like.

Processing continues at 1010 where the application causes the driving pattern data to be transmitted to an insurance processing system for further processing (e.g., such as for underwriting, risk analysis or other processing such as that described below in conjunction with FIGS. 13-19).

Pursuant to some embodiments, an application may be stored in, or accessible to, memory 508 of mobile device 500 which allows a user of mobile device 500 to interact with the application to transmit data and information about an accident, injury or loss to an insurance system 102. For example, in some embodiments, a user may activate an insurance application when an accident, injury or loss occurs, and for which insurance coverage may be sought. The insurance application prompts the user to provide detailed information about the event (which may vary based on the type of event). In some embodiments, the insurance application prompts the user to take one or more photos or videos associated with the accident, injury or loss to prove the extent of damage or loss. The data collected by the application is transmitted over a network to an insurance system 102 for further analysis. In some embodiments, the data is geotagged so that the insurer can identify the exact location and time of the claim. In this manner, insurers can more quickly act on claims, and can avoid or reduce the number of fraudulent claims submitted. In some embodiments, fraudulent claims can further be reduced by determining if a mobile device is in one location, but the alleged incident relating to a claim is at a second location.

Figure 11:
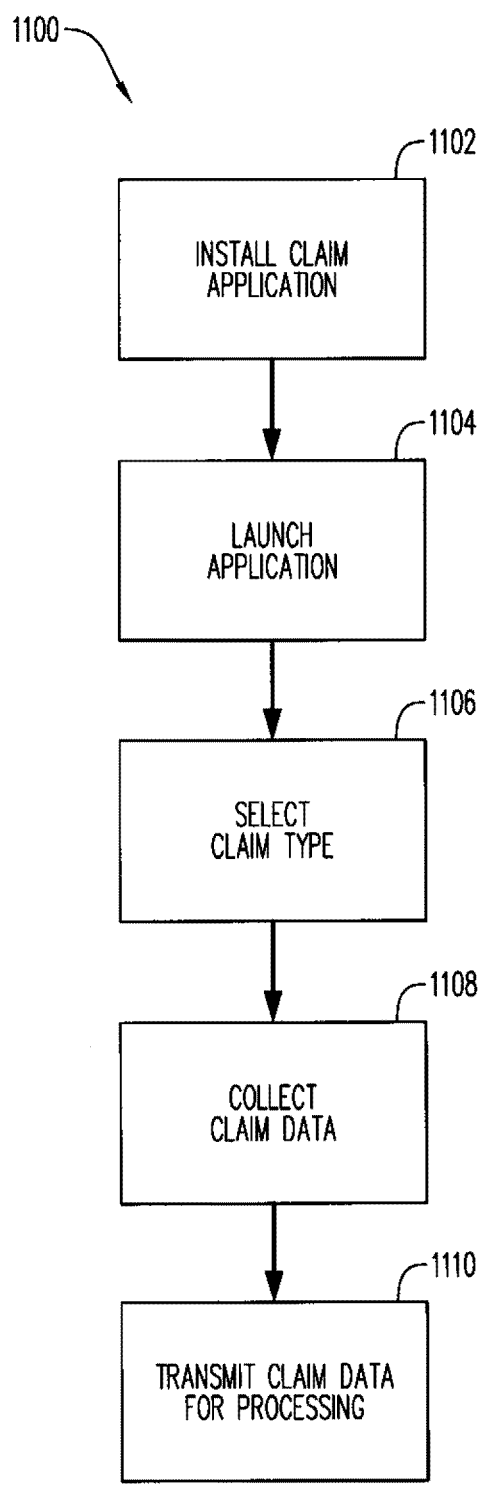
FIG. 11 is a flow diagram depicting a process for collecting and processing claim proof data pursuant to some embodiments.

Reference is now made to FIG. 11 where a claim proof and processing method 1100 is shown which may be performed using a mobile device such as a mobile device 500. Process 1100 may be performed using a mobile device such as the mobile device. As shown, processing begins at 1102 where a user of a mobile device 500 downloads and installs the claim proof application. This download and install may be performed from the mobile device 500 or from a desktop computer in communication with the mobile device 500. The application may be downloaded from the insurance system 102 or from an application marketplace. In some embodiments, the application may be installed at the request of an insurer, or as an option provided by an insurer so the user may qualify for more efficient claim processing as a result of the data collected by the user.

Processing continues at 1104 where the user launches the claim proof application (e.g., once a loss or event has occurred). Processing continues at 1106 where the user selects a claim type (e.g, such as an auto accident, a theft, an injury or the like). Processing continues at 1108 where the user, interacting with the application and using features of the mobile device (such as a voice recorder, camera, geo-location data, etc) collects claim data. For example, if the claim type is an auto accident, the user may be prompted to take one or more photos of any auto damage, as well as to enter data identifying the extent of the loss and circumstances surrounding the loss. Once sufficient data has been collected, processing continues at 1110 where the claim data is transmitted to an insurer system (such as system 102 of FIG. 1) for processing. Insurance processing may include processing as described below in conjunction with FIGS. 13-19.

Figures 12C, 12D:
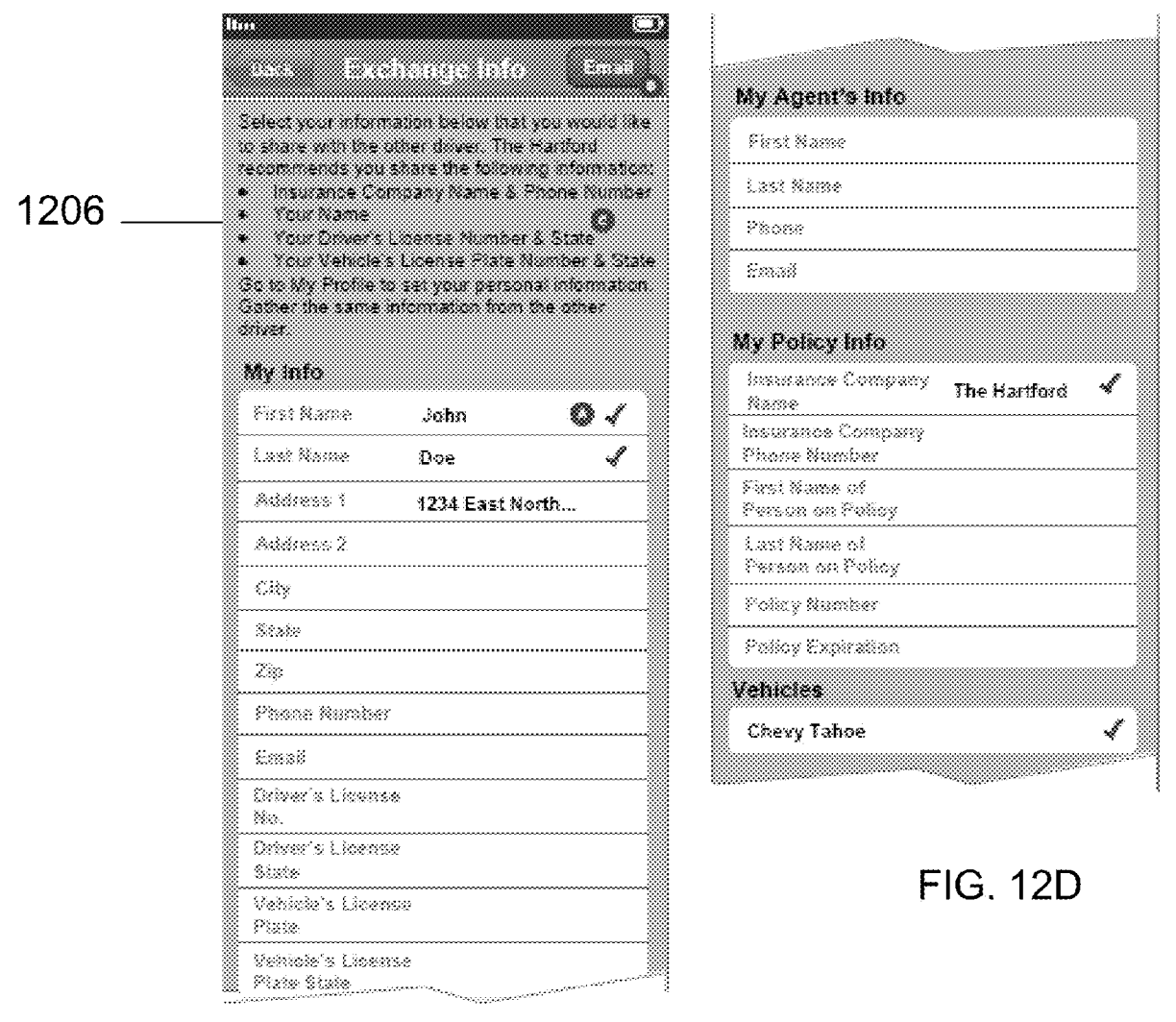
Figure 12I:
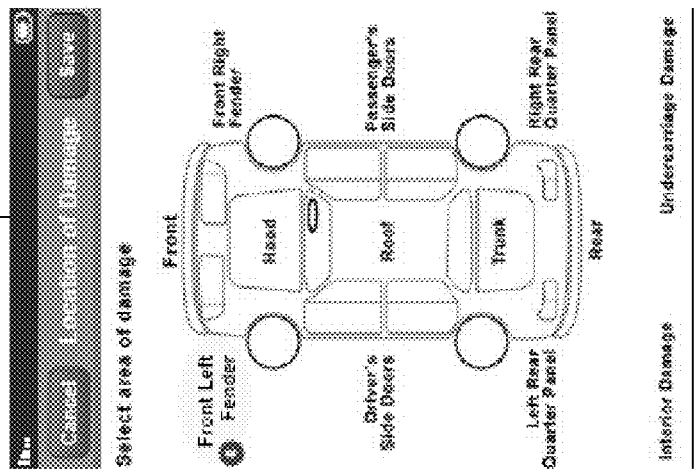
Figure 12H:
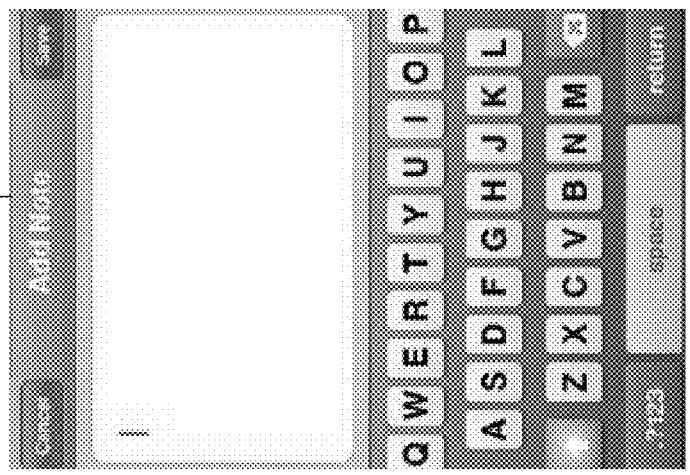

Reference is now made to FIGS. 12A-J, where a number of illustrative user interfaces depicting insurance application processing (e.g., as described in conjunction with FIGS. 7, 8 and 11) are provided. The user interfaces of FIGS. 12A-J may be displayed, for example, on a display device of a mobile device such as the device 500 of FIG. 5. A number of other user interfaces may be provided to allow user interaction with any of the flows or processes described herein, and the user interfaces of FIG. 12 are provided for illustration only. The user interfaces of FIGS. 12A-J depict an example series of interfaces that may be provided to a user who has had an accident. FIG. 12A shows a user interface 1200 that may be presented to a user who launches a mobile application pursuant to some embodiments and selects the option "I've Had an Auto Accident". The user interface 1200 includes a series of options or steps that the user may walk through in order to properly handle and report a claim associated with the accident.

Figure 12G:
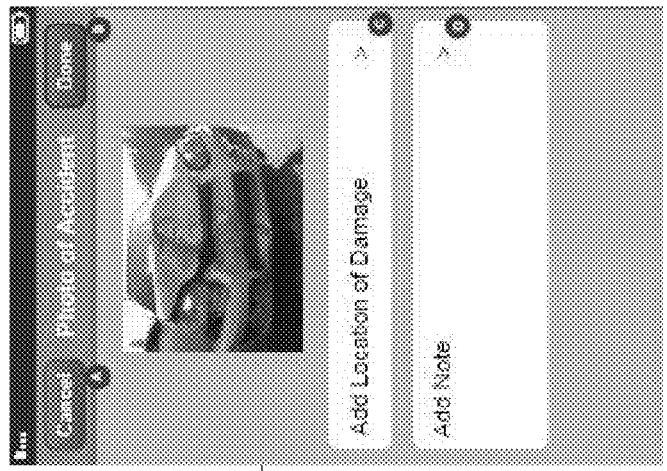
Figure 12J:
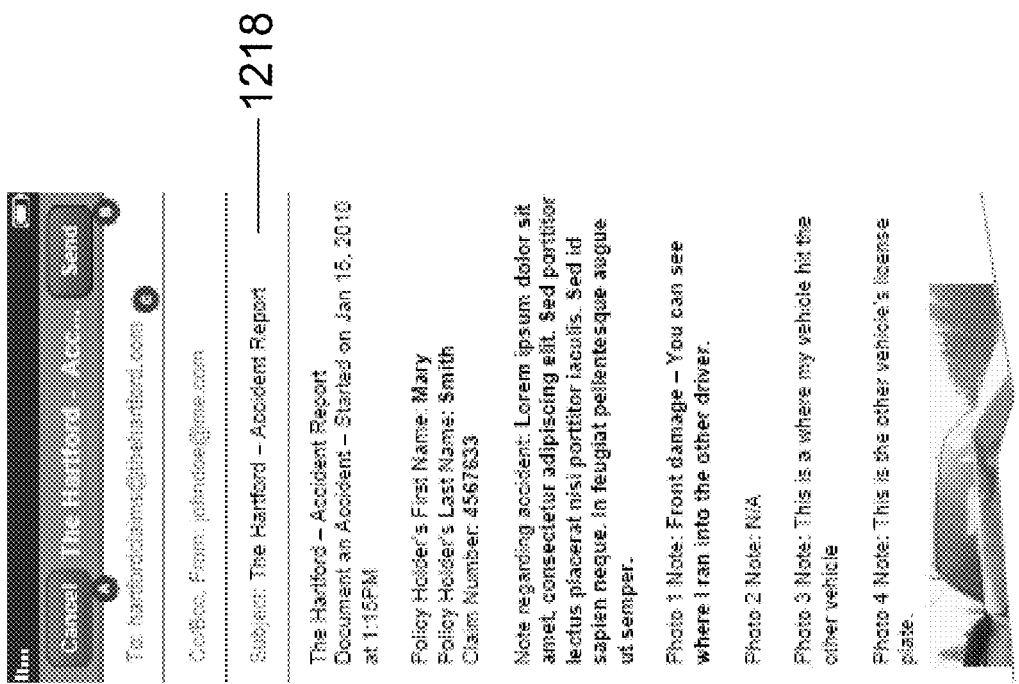

FIG. 12B depicts a user interface 1204 presenting an accident checklist that may be presented to the user so the user properly reports and handles the accident reporting. FIGS. 12C-D depict a user interface 1206 that is displayed in response to the user selecting the option of "Exchange Driver Info" and provides tips and instructions on what data to collect from the other driver. Some data may be prepopulated for the user to speed data collection. FIG. 12E depicts a user interface 1208 that prompts the user to provide information to document the accident, including taking photos and providing notes and details regarding the accident. FIG. 12F depicts a user interface 1210 that allows the user to select an option to email details of the accident to the insurance company. In some embodiments, the details may be wirelessly and automatically transmitted to the insurance company. FIG. 12G depicts a user interface 1212 that shows a photo taken by the mobile device which has been selected as representing the accident damage and location. A user may enter a note about the damage in a user interface 1214 (FIG. 12H) and may also indicate the location of the damage on the vehicle in a user interface 1216 (FIG. 12I). The full details entered by the user (including, in some embodiments, geocoded location and time data) may be transmitted to the insurance provider (e.g., as depicted in FIG. 12J as an email message transmitted to the insurer). Those skilled in the art will appreciate that other data entry, data configuration, and data collection screens may be provided to facilitate the collection and reporting of claim data.

Each of the mobile applications described herein may be in communication with one or more insurance processing systems such as the system 102 of FIG. 1. In addition to providing loss risk data as described above (e.g., in conjunction with route planning or the like), the systems may further operate or interact with data from the mobile applications to perform insurance policy underwriting, pricing, claim processing, policy renewal, risk analysis or the like. Features of some embodiments of insurance processing systems and environments will now be provided by reference to FIGS. 13-19. Each or any of the applications described above may provide data to, or receive data from, one or more of the insurance processing systems described below.

Figure 13:
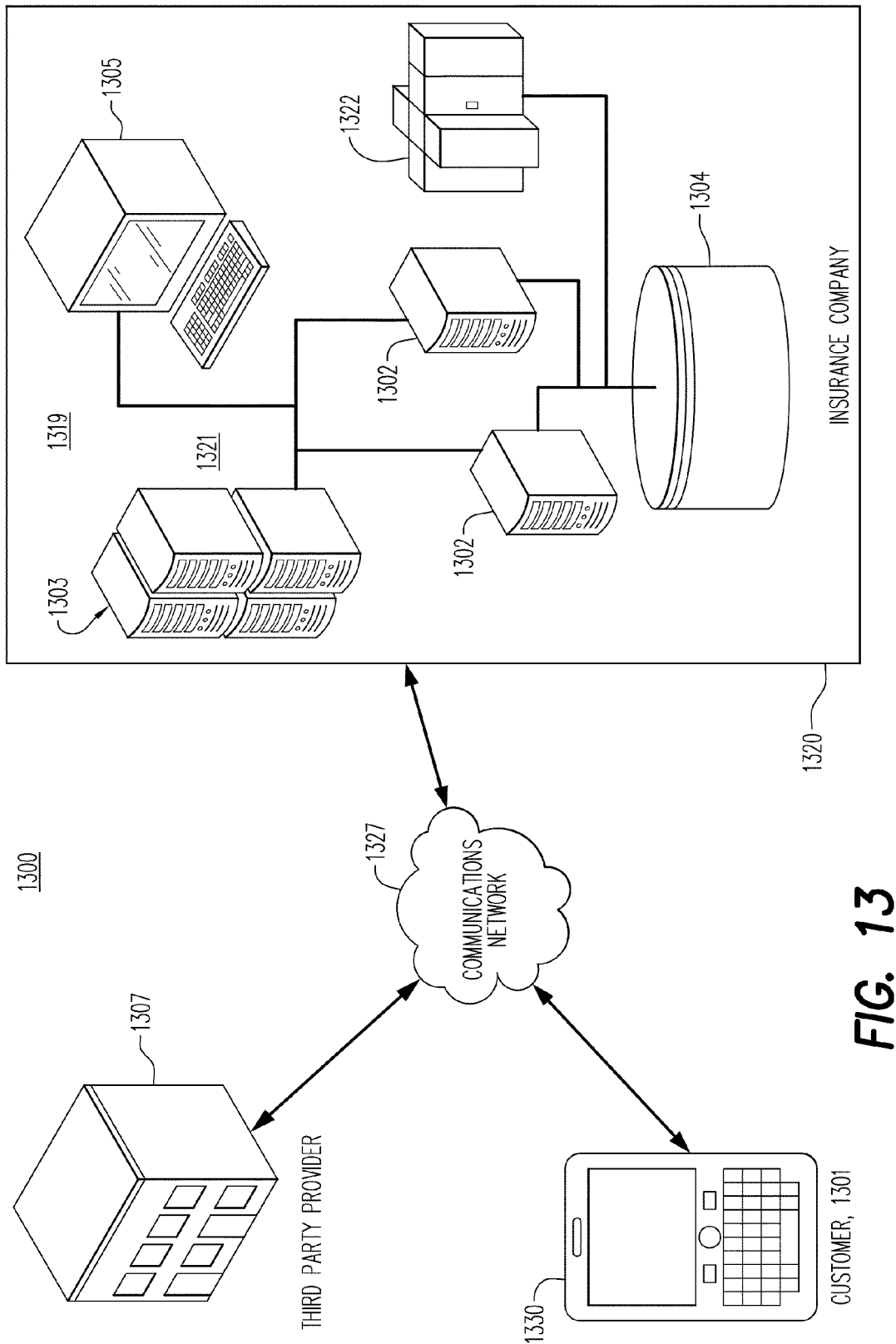
FIG. 13 is a block diagram of an insurance system pursuant to some embodiments.

FIG. 13 is a schematic diagram of a system 1300 for monitoring, evaluating, and providing feedback on insurance. In FIG. 13, insurance company 1320 provides customer 1301 with insurance coverage. The type of insurance provided by insurance company 1320 may be any type of insurance, such as general liability insurance, although the present invention is described primarily in terms of automobile insurance. Insurance company 1320 can simultaneously provide services to multiple customers, although only one customer 1301 is shown in FIG. 13 for clarity.

Mobile device 1330, pursuant to some embodiments, stores an application program that may be loaded onto the mobile device 1330 from an insurance company 1320 or from an application repository (e.g., such as Apple's App Store or the like). The application, when launched, prompts the customer 1301 from information used to interact with the insurance company 1320. A variety of different types of data and information may be provided from mobile device 1330 to insurance company 1320, including static data regarding the customer 1301, such as the customer's name, address, contact information, age, height, weight, policy information, etc. Other variable information may be provided (as described in each of the mobile application embodiments described above).

The data from mobile device 1330 is transmitted via communications network 1327 to insurance company 1320 for evaluation and processing. Third party provider 1307 can also be a source of information associated with customers and policies.

Insurance company 1320 has a computer system 1319 that includes application servers 1302, load balancing proxy servers 1303, data storage unit 1304, business logic computer 1322, and user interface module 1305 to perform risk evaluation and underwriting based on the collected data. Employees of the insurance company 1320 and other authorized personnel use user interface module 1305 to access the insurance company computer system. User interface module 1305 may be any type of computing device that is configured to communicate with other computer systems. User interface module 1305 may be connected directly to application server 1302, or may access an application server 1302 via the load balancing proxy servers 1303. User interface module 1305 may connect to load balancing proxy servers 1303 via a local area network, a private data link, or via the internet. Although depicted as being part of insurance company 1320 in FIG. 13, user interface module 1305 may be located remotely. The business logic computer 1322 is connected to the data storage unit 1304 and application servers 1302 over a local area network 1321, which may be part of communication system 1327. In addition, other network infrastructure, including, for example a firewall, backup servers, and back up data stores, may also be included in the system 1319, without departing from the scope of the invention. Communications over the local area network 1321 and/or over the Internet, in one implementation, may be encrypted. In addition, such communications, whether encrypted or not, may also be digitally signed for authenticating the source of the communications. The computer system 1319 may also include a certificate authority to authenticate one or more of the communications using public key infrastructure.

Based on data collected from the mobile device 1330 and any third party data sources, an evaluation module analyzes and evaluates data associated with a customer 1301. As used herein, a "module" may be implemented in software for execution by various types of processors. A n identified module of executable code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. In addition, entire modules, or portions thereof, may also be implemented in programmable hardware devices such as field programmable gate arrays, programmable array logic, programmable logic devices or the like or as hardwired integrated circuits.

A business logic module, implemented preferably in business logic computer 1322, is used to underwrite or alter insurance pricing for customer 1301 based on the received data. The business logic module may use predictive models, such as neural networks, Bayesian networks, and support vector machines, in performing the underwriting and premium adjustment. In one embodiment, the premium of an insurance policy is increased or decreased if data received from customer 1301 warrants. Instead of altering premium rates, other terms of the insurance policy can be altered, such as the policy deductible. In some embodiments, the premiums may be increased or decreased based on driving pattern data collected using the mobile device 1330 as described above in conjunction with FIG. 10. Further still, rates may depend on one or more loss risk scores calculated by the scoring engine 104 described in conjunction with FIG. 1.

In another scenario, insurance company 1320 awards customer 1301 with premium discounts, or other advantageous rewards, simply for operating certain mobile insurance applications as described above. Insurance company 1320 may award different discounts depending on the nature and amount of data provided by customer.

In one implementation, software operating on the application servers 1302 act merely as presentation and data extraction and conversion servers. All substantive business logic, including underwriting and pricing determinations, is carried out on the business logic computer 1322. In this implementation, the application servers 1302 obtain data from the data storage unit 1304 and the business logic computer 1322 and incorporate that data into web pages (or other graphical user interface formats). These web pages are then communicated by the application servers 1302 through the load balancing proxy servers 1303 to user interface module 1305 for presentation. Upon receiving input from user interface module 1305, the application server 1302 translates the input into a form suitable for processing by the business logic computer 1322 and for storage by the data storage unit 1304. In this implementation, the application servers can be operated by third parties, who can add their own branding to the web pages or add other customized presentation data. In the alternative, at least some of the business logic is also carried out by the application servers 1302. Application servers 1302 may also include a webserver for automatically recovering or retrieving data from local computer 1333.

In another implementation, the application servers 1302 are software modules operating on one or more computers. One of the computers on which the application servers 1302 are operating may also serve as the business logic computer 1322 and/or as a load balancing proxy server 1303.

In other implementations, the software operating on user interface module 1305 includes a thin or thick client application in addition to, or instead of web browser. The thin or thick client application interfaces with a corresponding server application operating on the application server 1302.

Figure 14:
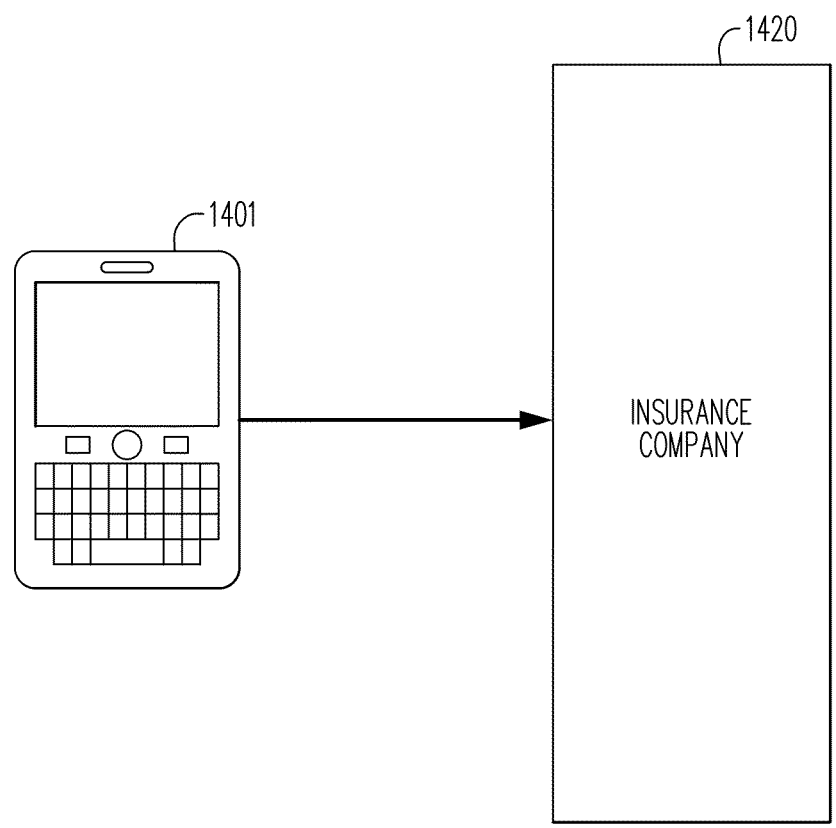
FIG. 14 is a block diagram of an insurance system receiving mobile device data pursuant to some embodiments.

FIG. 14 is a schematic diagram of an illustrative customer monitoring and evaluation system where a customer (operating a mobile device 1401) is insured by insurance company 1420. As customer 1401 operates and provides data using a mobile application (as described above) the mobile device transmits transmit data to the insurance company 1420.

The insurance company may perform, for example, a premium analysis which includes activities that potentially affect a customer's premium, deductible amount, discounts or credits, as well as large scale analysis to provide input into industry or occupation experience factors. The determination of premium and offering of discounts or credits may be performed once at underwriting time, regularly on an interval, continuously, in response to an event, or retroactively, as permitted by local, state, and/or federal regulations.

The analysis and decisions made by insurance company 1420 with regard to premium/service adjustments may be transmitted back to customer via the mobile device 1401. Insurance company 1420 may save the data and reports received from customer 1401, and the decisions that were made based upon them, in a data storage unit associated with the insurance company 1420 or in a separate data warehouse. This archived data may be used for future retrospective analysis, claims adjudication, and/or to support fraud investigation.

Figure 15:
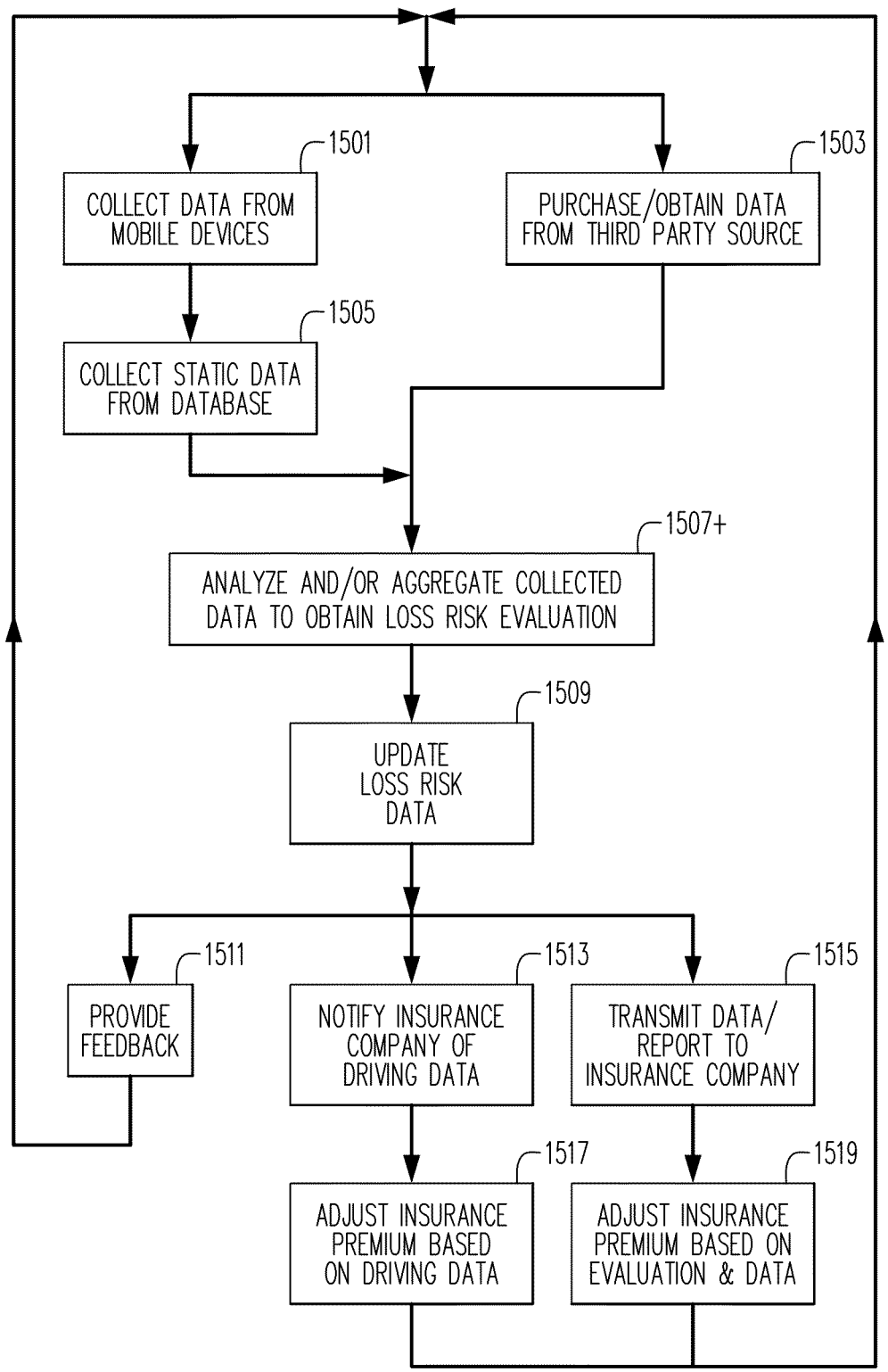
FIG. 15 is a flow diagram depicting a process for evaluating mobile device data pursuant to some embodiments.

FIG. 15 is a flow chart of exemplary steps in a method for evaluating data received from a mobile device operating one or more insurance applications as described above. For example, in embodiments where a mobile device is configured to collect driving pattern data associated with a user, the data may be collected, transmitted and used to evaluate insurance premiums and policy adjustments using the method of FIG. 15.

The method of FIG. 15 begins at 1501 by collecting data from mobile devices associated with an insured customer (or, in some embodiments, associated with a prospective insured customer). The data may include driving pattern data including speed, areas of operation, mileage traveled, time of operation, or other data collected by mobile computing devices as described above. The data may be transmitted to an insurance system for processing via wireless or cellular communication protocols. In some embodiments, the data may be transmitted automatically under control of a mobile application installed or operated on a mobile device associated with the customer.

In addition to mobile device data, static data may be collected at 1505. Static data may include personal information associated with a customer, such as their medical history, level of physical fitness, etc. In addition to or instead of collecting data from mobile devices and local static data servers, data may also be purchased or obtained from a third party at 1503. The purchased data may be used to supplement the mobile device data or may be used to validate or debug the system.

The data is analyzed, processed, and aggregated at 1507. The aggregated data may be generated into reports, which can then be provided to interested parties (at 1511 below). Data processing may include applying algorithms to the collected data, which may be in its raw form, to obtain values of interest. For example, raw sensor data may be noise filtered. In response to insured customer providing the data about their driving patterns or other driving related information, the insurance company can favorably alter the terms of the insurance policy, such as decreasing the premium or deductible.

At 1513, the insured customer provides the driving pattern data to the insurance company. In some embodiments, simply based on the customer's willingness to provide the data, and without receiving the actual data, the insurance company may grant discounts to the insured at 1517. In deciding to alter the terms of the insurance policy, the insurance company, or the third party evaluator, may compare the mobile device data, as determined from the mobile device, of the insured to a comparative baseline. The process of FIG. 15 may be repeated on a regular basis, and a similar process may be applied for a plurality of insured customers. In some embodiments, the process may be used to price and issue policies for new customers as well.

Reference is now made to FIG. 16 which is a high level flow chart of a method carried out by the system of FIG. 13 in processing requests for insurance. The method begins at 1602 with the receipt of a request to insure a driver. As described above, the request may be received by an insurance company 1320 from a mobile device 1330 (such as the mobile device 500 described in conjunction with FIGS. 5 and 6) or an agent/employee terminal. The system then requests and obtains information about the customer and the vehicle to be insured at 1604. The information is obtained in part through requests posed to the customer or insurance agent or employee assisting the customer. Additional information is obtained through the third party data vendors 1307 and from the central database 1304. Pursuant to some embodiments, many of the questions posed to the customer are presented to the consumer by an application on the mobile device which is provided by the insurance company.

In some situations, a prospective insured customer may be required to agree to provide driving pattern data associated with the customer's driving patterns in order to qualify for a policy (or to qualify for good driver discounts, etc). Insurance products that incorporate the use of collected driving pattern data in pricing and underwriting enable insurance companies to insure customers that might otherwise be outside of their appetite. That is, the risks presented by insuring a particular customer or vehicle operated by the customer may be too large for an insurance company to accept unless it is actively able to monitor the operation of a vehicle or driving characteristics of a customer. Thus, in one embodiment, after obtaining basic information about the vehicle and customer at 1604, the system 1320 determines whether driving pattern data is needed for making a final insurability decision at 1606. The system may determine that driving pattern data is unnecessary, for example, if the insurer determines that no amount of driving pattern data will bring the requested policy within the appetite of the insurance company, resulting in the request for being denied at 1616.

Insurance products using collected driving pattern data for adjusting premiums may also be used to reward customers that use, operate and maintain insured property safely. Thus, in some circumstances, collection of driving pattern data is not necessary, but instead is merely an option provided to customers that may lead to lower premiums. In such situations, the decision at 1606 may be skipped, and the method proceeds directly from the receipt of basic customer and vehicle information (at 1604) to determining whether driving pattern data is available (at 1608). Driving pattern data may be provided via a mobile device such as the mobile device 500 described above.

If at determination at 1608 indicates that existing driving pattern data is not available the insurance company, in one embodiment, may offer the customer insurance during a probationary period (at 1610) during which the insurance company can obtain baseline driving pattern data (at 1612) on which it can base its underwriting and pricing decision. Depending on the characteristics of the insured vehicle, the customer, and/or the data collected during the probationary period, the probationary period may vary in length, for example, from about one to about three months. For example, if the driving pattern data in a first month exhibits a great deal of variability, the period may be extended. The driving pattern data can include a number of parameters depending on the type of property to be insured. For example, for vehicles, the monitored parameters can include speed, acceleration, braking, turning speed, blinker usage, driving time of day, mileage, driving location, seat belt usage, and number of passengers. Raw vehicle operation data can be combined with location data to determine relevant speed limits, presence of stop signs, and other relevant location-based traffic laws, and a driver's adherence thereto. Other useful specific information may be derived from collected location data, including, for example, traffic patterns, road quality, incline and decline grades, crime rates, weather conditions and patterns, and accident rates. The parameters can also include data indicating the condition of the vehicle, including, without limitation, oil level, tire pressure, engine temperature, brake condition, fuel level, and the status of warning light indicators. The monitored parameters may also include activity levels associated with the vehicles, including, for example, how often items (e.g., radio, speed control, headlights, or alarm systems) within the vehicle are used as well occupancy and useage rates for the vehicle. The premium offered by the insurance company during the probationary period is likely higher than the premium that would be paid during a non-probationary coverage period, unless the data collected during the probationary period suggests the risks of issuing a non-provisional policy are substantially higher than expected based on the non-driving pattern related information collected prior to the probationary policy.

The insurance company 1320 then analyzes the driving pattern data made available at 1608 or collected at 1612 (at 1614). The exact analysis process, as described further below, is determined dynamically based on the driving pattern data collected, information about the customer, and/or information about the vehicle being insured. For example, the analysis may take into account different monitored parameters or take into account the same parameters to different extents. Preferably, the analysis is carried out using one or more predictive models, such as statistical models, neural networks, expert systems, or other forms of artificial intelligence.

Based on the analysis carried out at 1614, the insurance company 1320 decides whether to offer insurance to the customer under the terms requested by the customer (at 1616), and if so, calculates a premium for such a policy (at 1618). The premium may be calculated holistically for an entire policy, or separately for each coverage (e.g., collision, comprehensive, medical, uninsured motorist, physical damage, bodily injury, rental, and/or towing) requested in the policy. In one embodiment, the analysis of collected data at 1614, the decision to offer or deny insurance at 1616, and the determination of a premium at 1618 constitute a single process carried out by the computing systems of the insurance company 1320. In alternative implementations, the underwriting decision and the pricing calculation are carried out separately in series.

After determining a premium for the policy at 1618, the system forwards an offer for insurance to the mobile device 1330 or employee/agent terminal 1305 (at 1620). If the customer rejects the offer (at 1622), for example, due to the premium being higher than desired, or if the insurance company 1320 declines to offer insurance (at 1616), the process ends. If the offer is accepted (at 1622), the insurance company issues an insurance policy covering the customer and the vehicle (at 1624). After the policy is issued, the insurance company 1320, either directly or through a monitoring service, may continue to monitor the output of the sensors associated with the mobile device 1330. Based on the results of the monitoring, the insurance company 1320 occasionally or periodically may adjust the premium charged to the customer. The premium change, if any, preferably uses the same artificial intelligence used to set the initial premium. The premium change may affect the premium charged in future periods, in prior periods, e.g., through issuance of a refund or surcharge, or in a current period, depending on the specific implementation of the method. Alternatively, the premium change may only affect the premium charged for a renewal policy after the expiration of the current policy term.

While others have suggested utilizing data collected from sensors monitoring vehicles for insurance underwriting and pricing, the prior methods have failed to adequately take into account the fact that sensor data is not equally relevant to all insurance customers and all property requested to be insured. The following illustrative underwriting and premium pricing processes demonstrate that such distinctions can be made to achieve a more accurate insurance determination. The following processes are one example of pricing and underwriting processes that may be used in conjunction with some embodiments (in part or in whole). Further, features of the risk scoring and pricing methods described above may be used in conjunction with the processes of FIGS. 17 and 18 to perform pricing, premium adjustment, and underwriting.

Figure 17A:
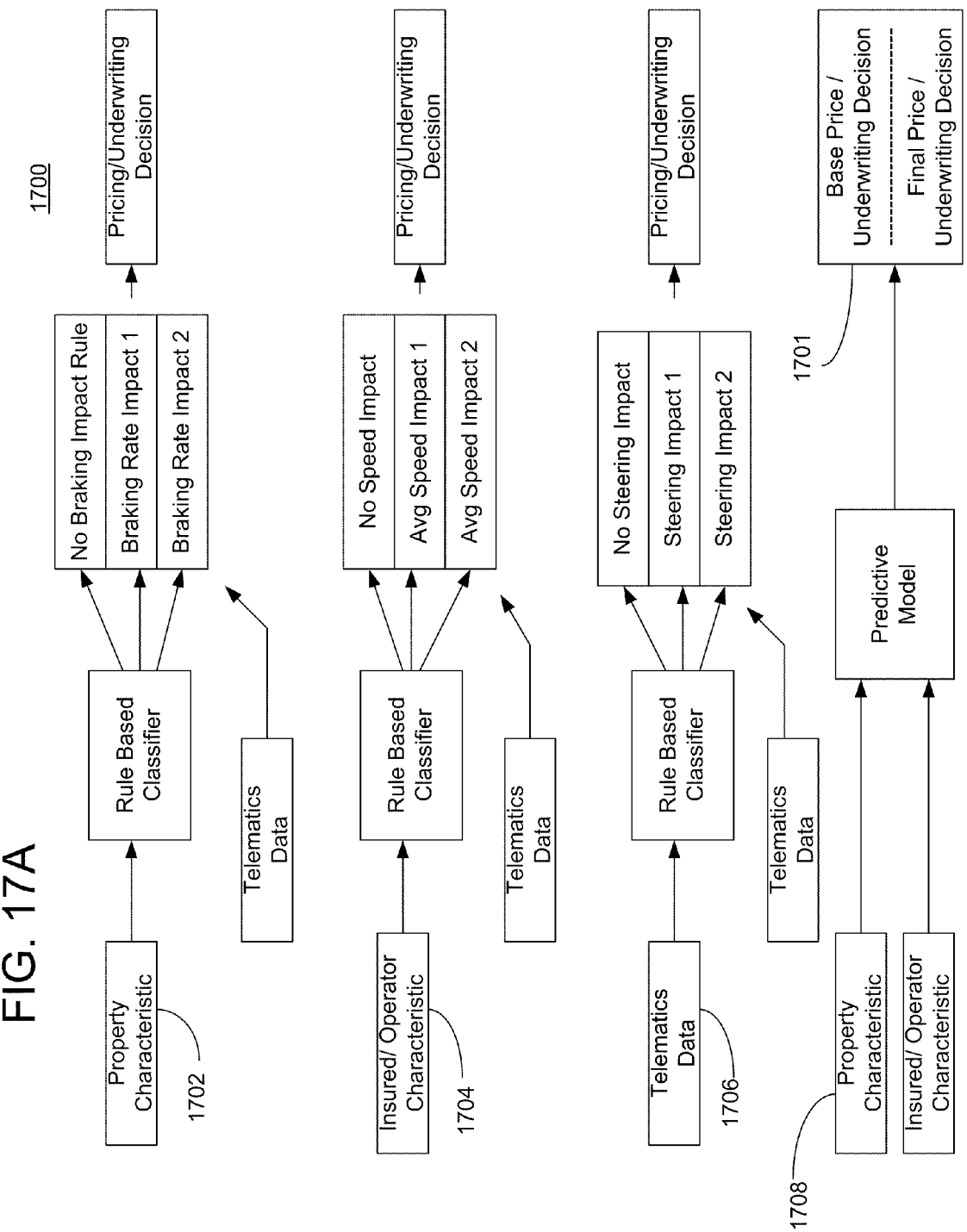
FIG. 17A is a diagram depicting a first underwriting and pricing process carried out by the system of FIG. 13 according to some embodiments.

FIG. 17A is a diagram depicting a first underwriting and pricing process 1700 carried out by the computer systems of the insurer 1320 of FIG. 13, according to an illustrative embodiment of the invention. The process 1700 generates an underwriting and a pricing decision 1701 for a request for personal lines auto insurance. The process 1700 is showed in simplified form for illustrative purposes. According to the process 1700, four separate underwriting and pricing determinations are made in independent process 1702, 1704, 1706, and 1708. The results of the four are combined to yield both a final underwriting decision and a final pricing decision 1701. Negative underwriting results from one process may be compensated for by positive underwriting results from other processes. Together, the processes determine which data parameters collected by sensors monitoring the vehicle are used in making the underwriting and pricing decisions and the weight each parameters plays in the decision making process.

The first process 1702 determines whether and to what extent a driver's braking behavior effects whether the vehicle should be insured, and at what cost. According to the process 1702, this determination is based on characteristics of the vehicle, for example, its size and its breaking system. Drivers with a habit of abrupt braking are at a greater risk of collisions resulting from a failure to stop. Larger vehicles require greater distances to stop and cause more damage upon impact. These factors, combined, make the risk associated with insuring larger vehicles with less efficient brakes greater than the risk associated with insuring smaller vehicles with better brakes. The risk posed by large vehicles can be mitigated, however, if the vehicle is driven with safer braking habits. The braking data may be collected using a mobile device such as the device 500 described above (e.g., via a Bluetooth® or other collection of braking data from an automobile computer system which is then forwarded to insurance company 1320 via the mobile device).

To translate these general principles into practical insurance decisions, a rule based classifier in the insurance company 1320 computer systems can be programmed with a set of rules that place a request to insure a vehicle into one of three categories: braking behavior is irrelevant, braking behavior is relevant, and braking behavior is important. For example compact cars with anti-lock brakes are assigned by the rule based classifier into the first category. Trucks with anti-lock brakes and mid-sized sedans with ordinary disk brakes fall into the second category. Trucks with standard disk brakes fall into the third category.

Based on the category into which the vehicle is categorized and actual data collected about the braking behavior of drivers of the vehicle, an underwriting and pricing impact is calculated. In one embodiment, the underwriting portion of the process 1702 includes a kill question. That is, there is a threshold, which, if met, would demand denial of the request for insurance coverage, regardless of what other parameters may be. For example, for vehicles in the third category, i.e., those with the greatest risk of collisions resulting from a failure to stop, an insurance request is "killed" if sensor data indicates that the vehicle stops abruptly, on average, more than once per day. If a request is killed, the customer is notified and further processing of the request is cancelled, avoiding unnecessary processing.

If the request for insurance survives the "kill question" of process 1702, a pricing result and an underwriting result are generated based on the category and observed braking behavior. For vehicles falling into the first category, braking behavior is ignored in making the pricing and underwriting decision, as braking behavior will have little impact on the risk posed by the vehicle. For vehicles that fall into the second category, safe braking habits may yield a small credit and a positive underwriting result. Poor braking habits may yield a small premium surcharge and a somewhat negative underwriting result. For vehicles in the third category, safe braking habits may yield a more significant premium credit, as a greater portion of the risk associated with insuring such a vehicle is managed well by the driver. Poor braking habits, if not sufficiently poor to surpass the "kill threshold" may result in a substantial premium surcharge and negative underwriting result.

While in the illustrative process 1702, a vehicle's size and braking system impact only the way in which the computer systems of the insurance company 1320 manipulates a single collected data parameter, i.e., braking behavior. The same factors may be used to dictate the way in which the computer systems of the insurance company 1320 manipulate other collected data parameters, including, for example, speed or acceleration. The rules used to assign a vehicle to a braking behavior category may be identical to those used to assign the vehicle to speed or acceleration categories. Alternatively, the business logic computer may implement separate classification rules for each collected data parameter. Particularly in this second case, the business logic computer may take one set of collected data parameters into account if the vehicle has a first characteristic (e.g., it has anti-lock brakes) and a second set of collected data parameters into account if the vehicle has a second characteristic (e.g., it has disc or drum brakes). Other vehicle characteristics that may be employed as determinants of the impact of various collected data parameters include, without limitation, vehicle safety ratings, engine size, color, cargo capacity, and age. In insuring buildings, characteristics of the buildings that may be used as determinants of the impact of collected data parameters include building age, construction, location, and use.

The second process 1704 determines if, and to what extent, the average speed at which a vehicle is driven impacts the insurance pricing and underwriting decision. In the illustrative process 1704, the determination is based on a characteristic of an owner seeking to insure the vehicle. Such characteristic might be, for example, the driver's age and/or driving record. These characteristics are analyzed by another rule-based classifier to assign insurance requests into three categories. In the first category, speed is considered irrelevant, in the second category, speed is relevant, and in the third category, speed is considered important. As in the first process 1702, the request for insurance is considered in light of the category and the actual data observed by the sensors monitoring the vehicle. Analysis of the actual vehicle speed may result in "killing" the request, or it may result in a range of pricing and underwriting results, as described above.

As with the first process 1702, the characteristic of the entity seeking to insure the vehicle, i.e., its owner and driver, may impact the way the computer systems of the insurance company 1320 manipulate multiple collected data parameters. For example, the age of the owner may also dictate the way the business logic computer takes into account the time of day during which the vehicle is driven and/or the acceleration behavior detected by sensors monitoring the vehicle. For example, for a vehicle owned by a minor, the business logic computer may ignore the time of day during which the vehicle is driven, consider the vehicle's speed (for example, the average speed, maximum speed, and/or a actual speed/posted speed limit differential) important, and the vehicle's acceleration only relevant. Alternatively, for a teen driver, number of passengers and the day of week and time of day of driving may be important. In contrast, for an elderly vehicle owner/operator, the business logic computer may ignore acceleration behavior, consider speed relevant, and time of day important. Thus, based on the value of this one characteristic of the entity seeking insurance, different sets of collected data parameters may be taken into account in making underwriting and pricing determinations. Additional characteristics of an entity that may be employed as determinants of the way in which the computer systems manipulate collected data parameters in making underwriting and pricing decisions include, without limitation, driving history, gender, and for commercial vehicles, the line of business in which the entity is involved.

The third process 1706 determines if, and to what extent, the steering behavior with which a vehicle is driven impacts the insurance pricing and underwriting decision. In the illustrative process 1706, the determination is based on sensor data collected from monitoring the vehicle. Relevant data parameters might include, for example, the speed at which the vehicle is driven. For example, erratic or frequent steering at high speeds may be indicative of aggressive highway lane changing or reckless turning.

Speed is analyzed by a third rule-based classifier to assign insurance requests into three steering behavior categories. For example, in one implementation, the third rule-based classifier assigns requests based on average speed. If average speed falls below 45 miles per hour, a vehicle is assigned to a first category. If average speed falls between 46 miles per hour and 60 miles per hour, the vehicle is assigned to a second category, and if the average speed exceeds 60 miles per hour, the vehicle is assigned to the third category. In an alternative implementation, the third rule-based classifier assigns requests based on the frequency of the vehicle speeding (i.e., driving above a posted speed limit). In another alternative implementation, the third rule-based classifier assigns requests based on the average speed of the vehicle in relation to the speed of nearby vehicles, determined, for example, by sonar, laser, radar, or other ranging technology incorporated in the vehicle.

Pursuant to some embodiments, the risk score calculated pursuant to some embodiments (and described above in conjunction with, e.g., FIG. 1) may be used as a factor, category or classifier in performing the analysis of FIG. 17.

In the first category, steering behavior is considered irrelevant, in the second category, steering behavior is relevant, and in the third category, steering behavior is considered important. Subsequently, the request for insurance is considered in light of the category and the actual vehicle steering behavior observed by the sensors monitoring the vehicle. Analysis of the actual steering behavior may result in "killing" the request, or it may result in a range of pricing and underwriting results, as described above. As with the other processes 1702 and 1704, the value of a collected data parameter may govern the application of, and weight assigned to more than one other collected data parameter. Additional data parameters that may be employed as determinants of the way in which the business logic computer 101 manipulates those data parameters or others in making underwriting and pricing decisions include, without limitation, driving location, how often the vehicle is used, and the environment, e.g., weather conditions, in which the vehicle is driven.

Finally, according to a fourth process 1708, a base price and underwriting determination are made based purely on information related to the customer and intended drivers of the vehicle and information about the vehicle itself. The information utilized for this process is obtained from the web pages presented by the insurance company 1320 along with information garnered from the third party data sources 1307 based on the information submitted through the web pages.

In a particular implementation, each process results in an absolute price determination and an underwriting score. So long as the sum of the underwriting scores stays within a specified range, the insurance company 1320 offers insurance coverage to the customer. If the number falls outside of the specified range, insurance coverage is denied. In determining the absolute costs for the first three processes 1702, 1704, and 1706, each category is associated with a multiplier. For example, the process 1702 may add a surcharge determined by the following equation: Surcharge=multiplier.times.$100*average number of abrupt braking incidents per day. As indicated above, in the first category, braking is deemed irrelevant, and therefore the multiplier associated with the first category is zero. The multiplier associated with the second category is 1.0 and the multiplier associated with the third category is equal to 2.0. The speed related surcharge is determined as follows: Surcharge=multiplier*$10.00*(average speed-55 mph). In this case, the multiplier associated with the first category is zero. The multiplier associated with the second category is 1.0, and the multiplier associated with the third category is 3.5. In alternative implementations, the categories may be associated with exponent values, log values, or other modifiers or functions to apply to the value of the data parameter in question instead of a simple multiplier.

In practice, an actual pricing and underwriting process may have fewer than four or more than four underwriting and pricing processes. In addition, while the processes 1702, 1704, 1706, 1708 describe assigning insurance requests to one of three categories, in practice, the processes may assign requests to one of four, five, ten, twenty or more categories. In addition, the equations for determining premium modifications may be substantially more complicated.

Figure 17B:
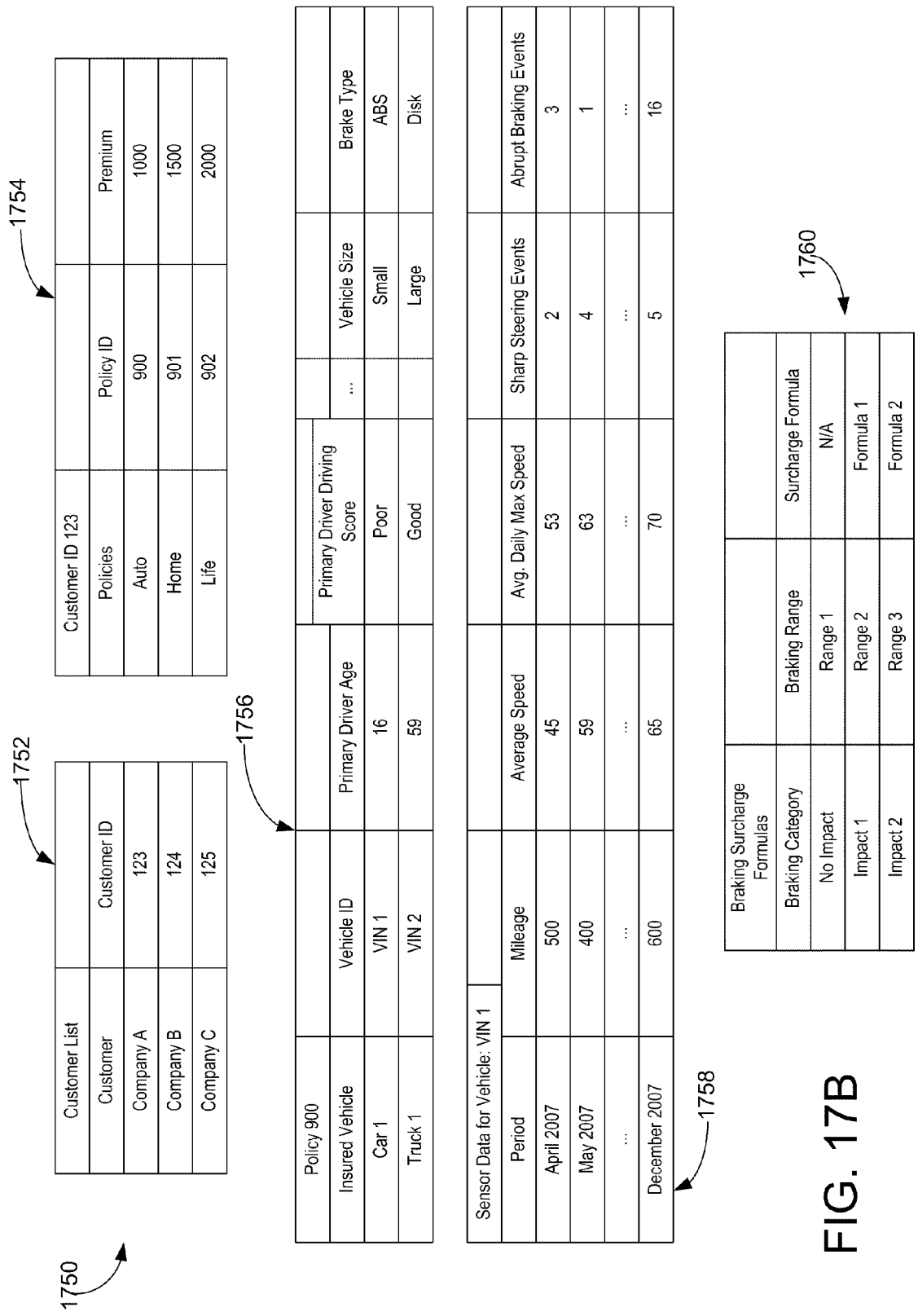
FIG. 17B is a diagram of illustrative data tables maintained by the database of FIG. 13 for implementing the process of FIG. 17A.

FIG. 17B depicts data tables 1750 maintained by the database 1304 of FIG. 13, for implementing the underwriting and pricing process 1700, according to an illustrative embodiment of the invention. The data tables 1750 include a customer list data table 1752, a customer policy data table 1754 for each customer, a policy data table 1756 for each issued policy, a sensor data table 1758 for each piece of insured property for which sensor data is collected, and formula tables 1760 for determining premiums based on the data stored in the remaining tables. The set of tables 1750 and data parameters within the data tables 1750 selected for depiction in FIG. 17B highlights the types of data and that may be stored within the database 1304 for use in the process 1700, and is in now way intended to be limiting of the types of data that may be stored, or the format in which is may be stored, in any given implementation of the system 1300. Similar data tables may be employed to implement the processes described below with respect to FIG. 18.

The customer list data table 1752 includes a list of the customers served by the insurance company with an associated customer ID used for identification purposes in the database. For each customer listed in the customer list data table 1752, the database 1304 includes a customer policy data table 1754. The customer policy data table 1754 lists the various policies issued to the customer along with a corresponding ID and premium value. In the illustrative customer policy data table 1754, the premium value is an annual premium value. Alternatively, the premium value may be stored for any desired period, including premium per day, per week, per month, or per quarter. In one implementation, the premium period is selected to correspond to the frequency with which the premium may be adjusted based on the collected sensor data. The premium is determined by the computer systems of the insurance company 1320 and forwarded to the database 1304 for storage.

For each policy, the database 1304 includes a policy data table 1756. The policy data table 1756 includes data describing the property covered by the policy, and if relevant, information about users of the property. Such data may include identifying information relevant to premium pricing. For example, for a vehicle, the policy data table 1756 identifies the make, model, value, prior damage, vehicle size, and braking technology employed by the vehicle. It also includes data about the primary driver of the vehicle, including his or her age and a characterization of their driving history.

The set of data tables 1750 stored in the database 1304 also includes sensor data tables 1758 for insured pieces of property. For vehicles, the sensor data table 1758 may be indexed by vehicle identification number. In the illustrative sensor data table 1758, data is stored on a period basis, for example, as aggregate information for each month of coverage. The sensor data table 1758 includes mileage data, average speed data, average daily maximum speed, a number of high acceleration events, and a number of abrupt braking events. This data may be fed directly from data uploaded from the sensors, or it may first be processed by the computer 1302 to generate the aggregate information.

The illustrative data tables 1750 also include formula data tables 1760 used to calculate premiums based on the data stored elsewhere in the database 1304. For example, to calculate the a surcharge resulting from braking behavior, a braking formula table 1760 includes a list of braking categories, with corresponding ranges that define membership in the category, as well as corresponding formulas for calculating surcharges based on membership in each respective category. During a pricing or underwriting decision, the computer 1302 retrieves the appropriate formulas from the formula tables 1760 to make its determination. In addition, as additional data is collected, the system can be retrained based on the new data, and new formulas can be stored in the formula data tables 1760. In alternative implementations, formulas are encoded directly in the software executed by the computer 1302.

As indicated above, the data tables 1750 described above are merely illustrative in nature. Various implementations may have fewer or more data tables storing fewer or more parameters without departing from the scope of the invention.

Figure 18:
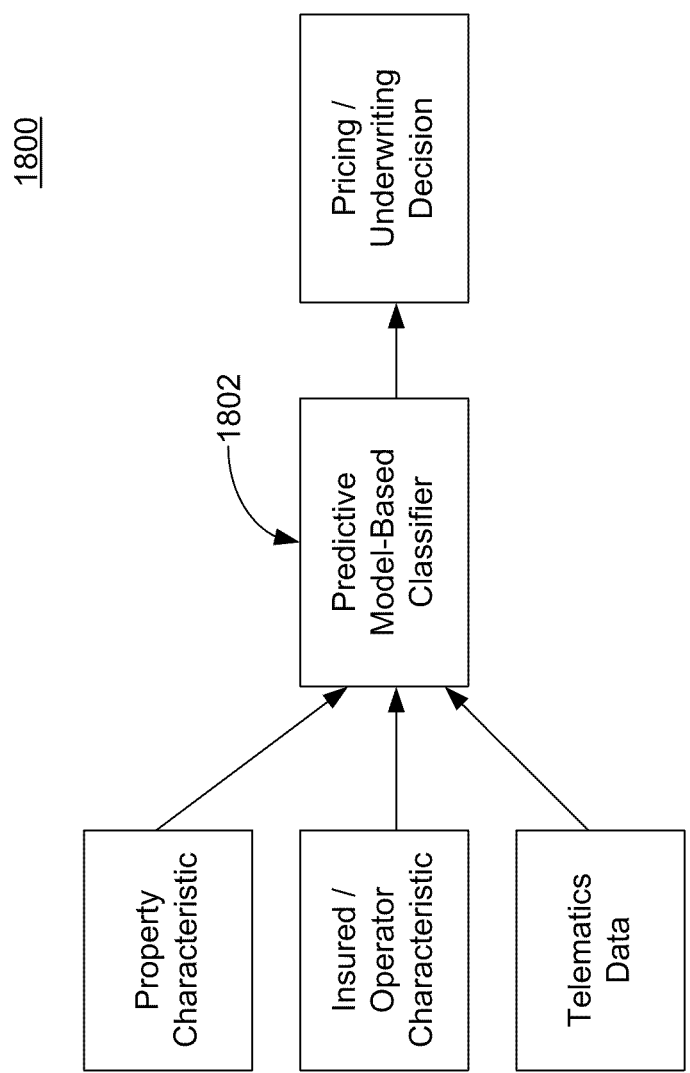
FIG. 18 depicts an illustrative underwriting and pricing process according to some embodiments.

FIG. 18 depicts a third illustrative underwriting and pricing process 1800, according to an illustrative embodiment of the invention. The process 1800 alters the way in which collected driving pattern data impacts an underwriting and pricing outcome based on one or more of characteristics of a customer or operator of a vehicle, and/or on one or more collected sensor data parameters. In the process 1800, a single predictive model 1802 directly outputs an underwriting and pricing result, without first outputting a classification. For example, the predictive model 1802 is programmed with a base premium price for each set of policy limit/deductible pairs made available to customers. Then, the predictive model 1802, using a clustering process, for example, an SVM, determines a set of previously issued coverages having risk profiles to which the requested policy is most similar. An SVM process iteratively separates elements of application in multidimensional space by identifying hyperplanes that maximizes distance between elements on either side of the hyperplanes. The process iterates to divide the elements into smaller and smaller groups. During this iterative clustering process, depending on which cluster an insurance request falls into at an early stage in the clustering process, different dimensions may be relevant in assigning the insurance request to a smaller cluster within that cluster.

After being assigned to a cluster, the loss history of the existing coverages in the cluster are compared to a loss history distribution of the entire universe of coverages. A premium for the new policy is set based on the base premium and where on the distribution of loss histories the assigned cluster falls.

Figure 19:
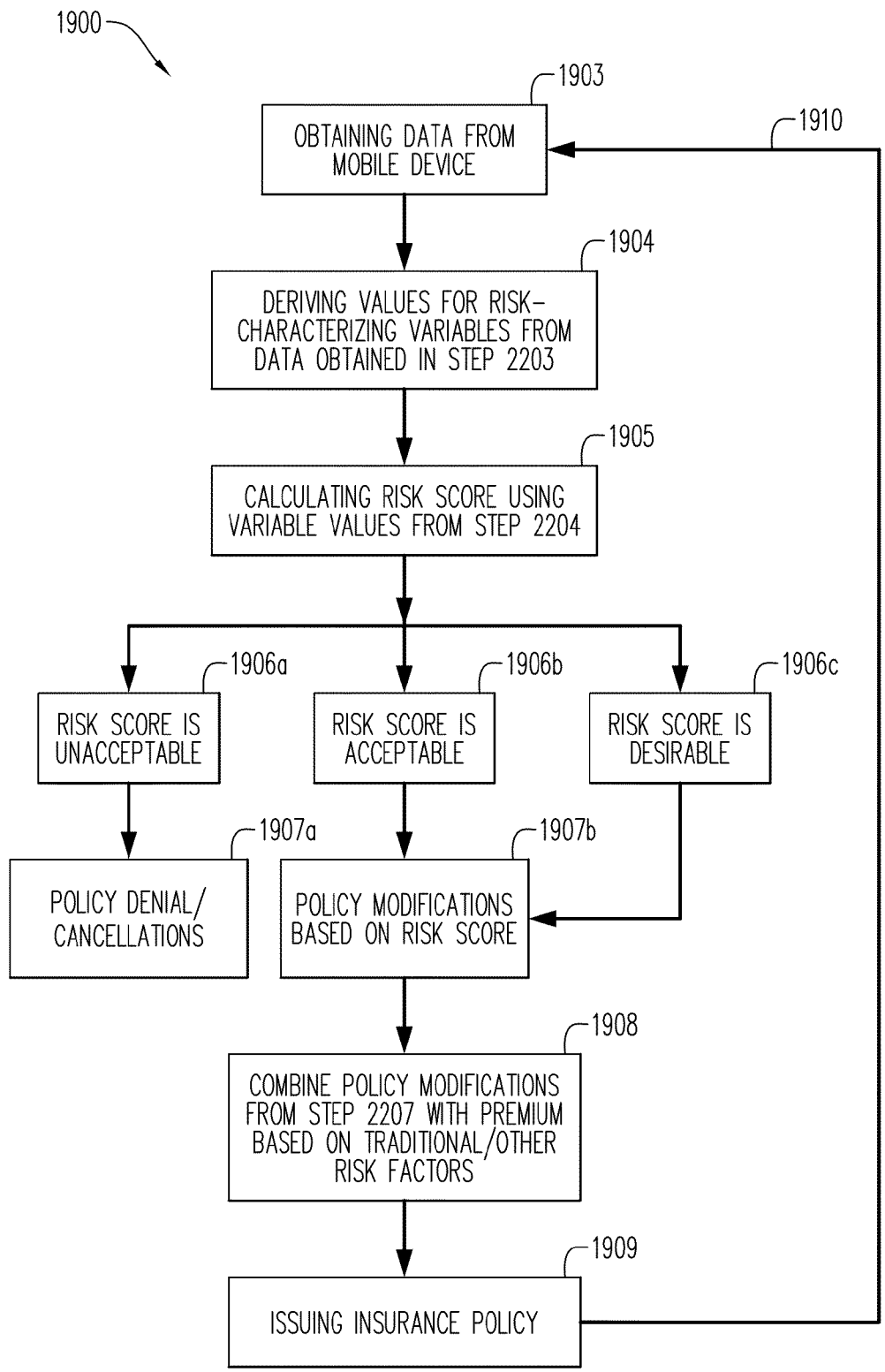
FIG. 19 is a flow diagram of a method of risk evaluation pursuant to some embodiments.

FIG. 19 shows a flowchart of a method of risk evaluation 1900, according to an illustrative embodiment of the invention. The risk evaluation method, in some embodiments, uses data received from a user operating a mobile device (such as the mobile device 500 described above). At step 1903, the insurance company obtains customer data related to the customer from a mobile device (and any external sources). These sources may include client questionnaires, driving pattern data collected by the mobile device 500, outside experts, or other external sources of information. Outside experts may include private research services, government agencies, or databases of collected information. The data may be collected by the insurance company in real-time, or at discrete time intervals throughout the term of the insurance policy.

Optionally at step 1904, values for intermediate variables that characterize risk are derived from the collected data. At step 1905, the intermediate variable values from step 1904 may be used to calculate a total risk score associated with the customer or insured vehicle. In one embodiment, the risk score is calculated by taking the weighted sum of the intermediate variable values from step 1904, where the weights are determined retrospectively e.g., using regression analysis from a database of insured data. Alternatively, the total risk score may be computed directly from the data collected at step 1903.

Depending on the value of the computed risk score, the risk score may be determined to be unacceptable (step 1906a), acceptable (step 1906b), or desirable (1906c). This determination may be done automatically by an insurance company computing system or program, such as insurance system computer 1302, or may be decided upon by an insurance agent or insurance company employee. Although there are only three categories shown in the figure, the risk score may be characterized into any number of categories, or may be considered a continuous real number.

If the risk score is decided to be unacceptable, then the customer may be denied an insurance policy at step 1907a. If a policy already exists, a renewal may be declined. If the risk score is decided to be acceptable or desirable, appropriate modifications, if any, to premiums based on the risk score may be determined at step 1907b. The premium may be reduced if the risk score is favorable, or it may be increased if the risk score is unfavorable (though still acceptable). The premium may not be altered at all if the risk score is moderate or inconclusive. Furthermore, different types of coverage policies, such as general liability or worker's compensation, may be selectively offered or denied in response to the risk score.

At step 1908, any modifications made in step 1907 may be combined with premium determinations made based on risk factors unrelated to the policy in a separate underwriting process. The final policy may then be issued at step 1909.

If the data collected at step 1903 changes during the term of an issued insurance policy at step 1910, the risk score may be reevaluated based on the new data. Accordingly, the insurance policy may be modified and reissued or even canceled. Reevaluation of risk may occur in real-time as data is collected in real-time, or may occur at discrete time intervals throughout the term of the policy. Steps 1903-1909 may thus be repeated many times during the term of an insurance policy.

Thus, embodiments of the present invention may improve the information available to vehicle operators to alert them of higher risk areas as well as the information available to insurers to allow them to price, analyze and underwrite policies. Although the present invention has been described in connection with specific exemplary embodiments, it should be understood that various changes, substitutions, and alterations apparent to those skilled in the art can be made to the disclosed embodiments without departing from the spirit and scope of the invention as set forth in the appended claims.

What is claimed is:

1. A computer system for facilitating of vehicle routing with reduced risk, comprising:
    a data storage device for storing, updating and providing access to vehicle loss risk score data;
    a computer processor for executing program instructions and for retrieving the vehicle loss risk score data from the data storage device;
    a memory, coupled to the computer processor, for storing program instructions for execution by the computer processor;
    a geocoding engine comprising program instructions stored in the memory for geocoding historical loss data, current vehicle loss data, and a plurality of vehicle loss risk factors;
    a scoring engine comprising program instructions stored in the memory for calculating a vehicle loss risk score for each of a plurality of geographical locations based on said historical loss data, said current loss data, and said plurality of vehicle loss risk factors, including computing a result of an algorithm including as factors an average claim severity, an average claim frequency, a population density, and day of week risk factor, wherein said vehicle loss risk score for each of said plurality of geographical locations is stored in said data storage device;
    a communication device, coupled to the computer processor, to (i) receive actual trip route data automatically generated and transmitted by a plurality of mobile devices, the trip route data generated by GPS receivers and accelerometers, associated with a driver, the actual trip route data including a set of geographical locations through which the mobile device traveled over a period of time; (ii) receive the current loss data comprising new vehicle loss claim data and accident event data; and (iii) output vehicle loss risk score data,
    one or more application programming interfaces configured to expose some or all of the scoring data to an external mapping service to facilitate route selection based on mapping data from the external mapping service,
    the received actual trip route data and the loss risk scores associated with said set of geographical locations; and
    a display device to display routing options for selection based on the vehicle loss risk scores.

2. The computer system of claim 1, wherein said communication device receives a user location from a user operating the mobile device, said scoring engine further comprising program instructions to calculate a loss risk score for said user location.

3. The computer system of claim 1, said scoring engine further comprising program instructions stored in the memory for determining at least a portion of said loss risk score using data mining techniques including text mining to locate, identify and extract location and risk-relevant data for use by the scoring engine.

4. The computer system of claim 3, wherein said communication device transmits said loss risk score in a format for display by said mobile device.

5. The computer system of claim 4, wherein said format is as a map overlay format.

6. The computer system of claim 5, wherein said communication device receives a route request from a user operating a mobile device, said route request specifying a destination, said scoring engine further comprising program instructions to calculate a trip risk score associated with at least one route to said destination.

7. The computer system of claim 6, said scoring engine further comprising program instructions to calculate a first trip risk score associated with a first route to said destination, and a second trip risk score associated with a second route to said destination, one of said routes having a lower trip risk score.

8. The computer system of claim 6, wherein said communication device transmits said trip risk score associated with each of said routes in a format for display by said mobile device.

9. The computer system of claim 1, wherein said plurality of loss risk factors include variable data from public data sources including a weather condition data source and a traffic condition data.

10. The computer system of claim 1, wherein said calculating a loss risk score for each of a plurality of geographical locations based on said historical loss data and said plurality of loss risk factors includes computing a result of a function involving a user generated risk factor.

11. The computer system of claim 1, wherein said geographical locations are identified by street-level geocode data.

12. The computer system of claim 11, wherein said loss risk score is calculated for a plurality of street intersections.

13. The computer system of claim 1, further comprising a claims processing module, the claims processing module comprising program instructions for receiving notice of loss information associated with a claim.

14. The computer system of claim 13, wherein said claims processing module is coupled to said communication device, said communication device receiving said notice of loss information from a mobile device.

15. The computer system of claim 13, wherein said notice of loss information received from said mobile device includes data collected from a location associated with said notice of loss, said collected data including at least one of: a timestamp, geolocation data, a picture, a voice recording, and a description of said loss.

16. The computer system of claim 14, wherein said mobile device is a mobile device associated with a policy holder submitting said notice of loss.

17. The computer system of claim 16, said communication device receiving independent data associated with said notice of loss, said independent data received from a second mobile device operated by a user other than said policy holder.

18. The computer system of claim 14, wherein said notice of loss information is provided to said scoring engine to update said loss risk score for said location associated with said notice of loss.

19. A computer-implemented method for facilitating vehicle routing with reduced risk, comprising:
retrieving vehicle loss risk score data from a data storage device;
geocoding, by a geocoding engine computer processor, historical loss data, current loss data, and a plurality of loss risk factors;
calculating, by a scoring engine, a vehicle loss risk score for each of a plurality of geographical locations based on said historical loss data, the current loss data, and said plurality of loss risk factors, including computing a result of an algorithm including as factors an average claim severity, an average claim frequency, and a day of week risk factor, wherein said vehicle loss risk score for each of said plurality of geographical locations is stored in said data storage device;
receiving, by a communication device, actual trip route data automatically generated and transmitted by a plurality of mobile devices, the trip route data generated by GPS receivers and accelerometers, associated with drivers, the actual trip route data including a set of geographical locations through which the mobile device traveled over a period of time, and the current loss data comprising new loss claim data and accident event data;
outputting, by the communication device, vehicle loss risk score data,
via one or more application programming interfaces exposing some or all of the scoring data to an external mapping service to facilitate route selection based on mapping data from the external mapping service,
the received actual trip route data and the vehicle loss risk scores associated with said set of geographical locations; and
displaying on a display device routing options and vehicle loss risk score data associated with the routing options.

20. The method of claim 19, wherein said geographical locations are identified by street-level geocode data.

21. The method of claim 20, wherein said loss risk score is calculated for a plurality of street intersections, the selected vehicle property characteristic category comprises a selected vehicle braking rate impact category, and the predictive model uses a clustering process to determine a set of previously issued coverages having similar risk profiles.

22. A non-transitory, computer-readable medium storing program instructions adapted to be executed by a computer processor to perform a method for facilitating vehicle routing with reduced risk, said method comprising:
retrieving vehicle loss risk score data from a data storage device;
geocoding, by a geocoding engine computer processor, historical loss data, current loss data comprising new loss claim data and accident event data, and a plurality of vehicle loss risk factors;
calculating, by a scoring engine, a vehicle loss risk score for each of a plurality of geographical locations based on said historical loss data and said plurality of loss risk factors, including computing a result of an algorithm including as factors an average claim severity, an average claim frequency, and a day of week risk factor, wherein said loss risk score for each of said plurality of geographical locations is stored in said data storage device;

receiving, by a communication device, actual trip route data automatically generated and transmitted by a mobile device associated with an entity, said actual trip route data generated at least in part by GPS receivers and accelerometers and including a set of geographical locations through which the mobile device traveled over a period of time;

outputting, by said communication device, vehicle loss risk score data, via one or more application programming interfaces exposing some or all of the scoring data to an external mapping service to facilitate route selection based on mapping data from the external mapping service, said received actual trip route data and said vehicle loss risk scores associated with said set of geographical locations; and displaying on a display device route selection options associated with the vehicle loss risk scores.

23. The medium of claim 22, wherein said geographical locations are identified by street-level geocode data.

24. The medium of claim 23, wherein said loss risk score is calculated for a plurality of street intersections.

* * * * *